(12) United States Patent
Stoltefuss et al.

(10) Patent No.: US 6,696,451 B1
(45) Date of Patent: Feb. 24, 2004

(54) DIHYDROPYRIMIDINES

(75) Inventors: Jürgen Stoltefuss, Haan (DE); Siegfired Goldmann, Wuppertal (DE); Thomas Krämer, Wuppertal (DE); Karl-Heinz Schlemmer, Wuppertal (DE); Ulrich Niewöhner, Wermelskirchen (DE); Arnold Paessens, Haan (DE); Erwin Graef, Velbert (DE); Stefan Lettmann, Wuppertal (DE); Karl Deres, Bad Bodendorf (DE); Olaf Weber, West Haven, CT (US); Jörn Stölting, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/673,592

(22) PCT Filed: Apr. 7, 1999

(86) PCT No.: PCT/EP99/02344

§ 371 (c)(1),
(2), (4) Date: Oct. 18, 2000

(87) PCT Pub. No.: WO99/54326

PCT Pub. Date: Oct. 28, 1999

(30) Foreign Application Priority Data

Apr. 18, 1998 (DE) .......................... 198 17 264

(51) Int. Cl.⁷ ..................... C07D 401/04; A61K 31/444
(52) U.S. Cl. .................. 514/256; 544/328; 544/333
(58) Field of Search ................. 544/328, 333; 514/256

(56) References Cited

U.S. PATENT DOCUMENTS

| | | | |
|---|---|---|---|
| 3,787,444 A | 1/1974 | Gosteli | 260/327 |
| 3,956,395 A | 5/1976 | Meyer | 260/607 |
| 4,727,073 A | 2/1988 | Takaya et al. | 514/252 |
| 4,822,798 A | 4/1989 | Stoltefuss et al. | 514/255 |

FOREIGN PATENT DOCUMENTS

| | | | | |
|---|---|---|---|---|
| EP | 0103796 | 3/1984 | ......... | C07D/239/20 |
| EP | 0169712 | 1/1986 | ......... | C07D/239/30 |
| JP | 60185764 | 9/1985 | ......... | C07D/213/70 |
| WO | 9011281 | 10/1990 | ......... | C07D/471/04 |
| WO | 9821199 | 5/1998 | ......... | C07D/401/00 |

OTHER PUBLICATIONS

Douglas, Jr. Introduction to Viral Diseases, Cecil Textbook of Medicine, 20th Edition, vol. 2, pp. 1739–1742, 1996.*
Adler, R., and Becker, H.–D., "Zur Slektiven Oxydation von Benzylalkoholen", Acta Chem. Scand., 15(4): 849–852 (1961).
Borrmann, D., "Umsetzungen von Diketen mit Alkoholen, Phenolen und Mercaptanen", in Houben–Weyl, Methoden der Organischen Chemie, vol. 7(4), pp. 230–232 (1968).
Fife, W. K., "Regioselective Cyanation of3–Substituted Pyridine 1–Oxides¹", Heterocycles, 22(1):93–96 (1984).
Glickman, S. A., and Cope, A. C., "Structure of β–Amino Derivatives of α, β–Unsaturated Lactones and Esters", J. Am. Chem. Soc., 67: 1017–1020 (Jun. 1945).
Harris, T. D., and Roth, G. P., "Ortho Lithiation via a Carbonyl Synthon", J. Org. Chem., 44(12): 2004–2007 (1979).
Jones, G., "The Knoevenagel Condensation" in Organic Reactions, vol. 15, Chapter 2, John Wiley & Sons, Inc. eds., New York, London, Sydney (1967) pp. 205.
Korba, B. E., and Gerin, J. L., "Use of a standardized cell culture assay to assess activities of nucleoside analogs against hepatitis B virus replication", Antiviral Res., 19:55–70 (1992).
Miyano, M. Muraki, S., Kusunoki, T., Morita, T., and Matsui, M., "Syntheses of several new compounds related to rotenoids (benzalacetones, o–benzyloxypehylacetonitrile, and chromans)", Heterocycles Compounds, 37:13929c (1963).
Oikawa, Y., Sugano, K., and Yonemitsu, O., "Meldrum's Acid Organic Synthesis. 2. A General and Versatile Synthesis of β–Keto Esters", J. Org., Chem., 43(10):2087–2090 (1978).
Papadopoulos, E. P., Jarrar, A., and Issiorides, C. H., "Oxidations with Manganese Dioxide", J. Org. Chem., 31:615–616 (Feb. 1966).

(List continued on next page.)

Primary Examiner—Deepak Rao

(57) ABSTRACT

The invention relates to compounds of the general formulae (I) and (Ia)

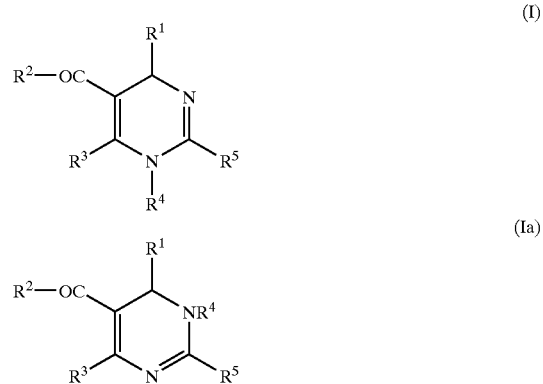

The invention furthermore relates to processes for preparing the compounds of the formulae (I) and (Ia) and to their use as medicaments, in particular for the treatment and prophylaxis of hepatitis B.

12 Claims, No Drawings

OTHER PUBLICATIONS

Sakamoto, T., Kaneda, S., Nishimura, S., and Yamanaka, H., "Site–Selective in the Cyanation of 3–Substituted Pyridine 1–Oxides with Trimethylsilanecarbonitrile", Chem. Pharm. Bull., 33(2): 565–571 (1985).

Sells, M. A., Chen, M.–L., and Acs, G., "Production of Hepatitis B Virus Particles in Hep G2 Cells Transfected with Cloned Hepatitis B Virus DNA", Proc. Natl. Acad. Sci. USA, 84: 1005–1009 (Feb. 1987).

Johnson, C. D., Katritzky, A. R., and Viney, M., "The Mechanism of the Electrophilic Substituion of Heteroaromatic Compounds. Part VII.1 The Nitration of Pyridines in the α–Position and Rules for the Nitration of Substituted Pyridines", J. Chem. Soc. (B): 1211–1213 (1967).

Troschutz, R., and Karger, A., "Versatile Synthesis of 6–Substituted 8–Deazapteridine–2,4–diamines. Formal Total Synthesis of 8,10–Dideazaminopterin", J. Heterocyclic Chem. 33: 1815–1821 (Nov.–Dec. 1996).

* cited by examiner

DIHYDROPYRIMIDINES

This application is a 371 of PCT/EP99/02344 filed Apr. 7, 1999.

The present invention relates to novel dihydropyrimidine compounds, to processes for their preparation and to their use as medicaments, in particular for the treatment and prophylaxis of hepatitis B.

Dihydropyrimidines having cardiovascular action are already known from the publication EP 103 796 A2.

The present invention now provides novel dihydropyrimidine compounds of the general formula (I)

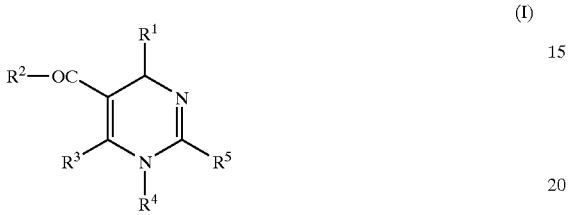

or their isomeric form (Ia)

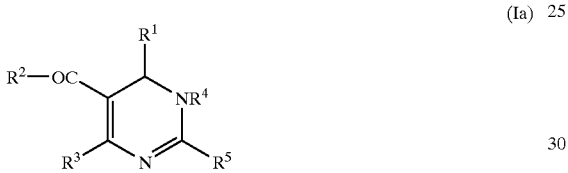

in which $R^1$ represents phenyl, furyl, thienyl, triazolyl, pyridyl, cycloalkyl having 3 to 6 carbon atoms or represents radicals of the formulae

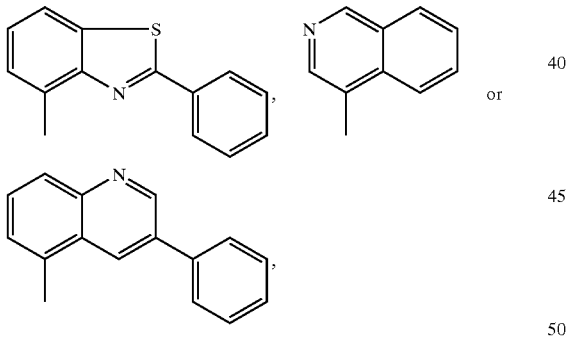

where the abovementioned ring systems are optionally mono- or polysubstituted by identical or different substituents selected from the group consisting of halogen, trifluoromethyl, nitro, cyano, trifluoromethoxy, carboxyl, hydroxyl, $(C_1-C_6)$-alkoxy, $(C_1-C_6)$-alkoxycarbonyl and $(C_1-C_6)$-alkyl, which for its part may be substituted by aryl having 6 to 10 carbon atoms or halogen, and/or the ring systems mentioned are optionally substituted by groups of the formulae —S—$R^6$, $NR^7R^8$, CO—$NR^9R^{10}$, $SO_2$—$CF_3$, and —A—$CH_2$—$R^{11}$, in which $R^6$ represents phenyl which is optionally substituted by halogen, $R^7$, $R^8$, $R^9$ and $R^{10}$ are identical or different, and each represents hydrogen, phenyl, hydroxyl-substituted phenyl, hydroxyl, $(C_1-C_6)$-acyl or $(C_1-C_6)$-alkyl, which for its part may be substituted by hydroxyl, $(C_1-C_6)$-alkoxycarbonyl, phenyl or hydroxyl-substituted phenyl, A represents a radical O, S, SO or $SO_2$, $R^{11}$ represents phenyl which is optionally mono- to polysubstituted by identical or different substituents selected from the group consisting of halogen, nitro, trifluoromethyl, $(C_1-C_6)$-alkyl and $(C_1-C_6)$-alkoxy, $R^2$ represents a radical of the formula —$XR^{12}$ or —$NR^{13}R^{14}$, in which X represents a bond or oxygen, $R^{12}$ represents hydrogen, straight-chain or branched $(C_1-C_6)$-alkoxycarbonyl or a straight-chain, branched or cyclic saturated or unsaturated $(C_1-C_8)$-hydrocarbon radical which optionally contains one or two identical or different hetero chain members from the group consisting of O, CO, NH, —NH—$(C_1-C_4)$-alkyl, —N—$((C_1-C_4)$-alkyl$)_2$, S and $SO_2$ and which is optionally substituted by halogen, nitro, cyano, hydroxyl, aryl having 6 to 10 carbon atoms or aralkyl having 6 to 10 carbon atoms, heteroaryl or a group of the formula —$NR^{15}R^{16}$, in which $R^{15}$ and $R^{16}$ are identical or different, and each represents hydrogen, benzyl or $(C_1-C_6)$-alkyl, $R^{13}$ and $R^{14}$ are identical or different, and each represents hydrogen, $(C_1-C_6)$-alkyl or cycloalkyl having 3 to 6 carbon atoms, $R^3$ represents hydrogen, amino or represents a radical of the formula

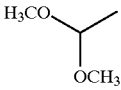

or represents formyl, cyano, trifluoromethyl or pyridyl, or represents a straight-chain, branched or cyclic saturated or unsaturated hydrocarbon radical having up to 8 carbon atoms which is optionally mono- or polysubstituted by identical or different substituents from the group consisting of aryloxy having 6 to 10 carbon atoms, azido, cyano, hydroxyl, carboxyl, $(C_1-C_6)$-alkoxycarbonyl, a 5- to 7-membered heterocyclic ring, $(C_1-C_6)$-alkylthio and $(C_1-C_6)$-alkoxy, which for its part may be substituted by azido or amino, and/or is substituted by triazolyl, which for its part may be substituted up to 3 times by $(C_1-C_6)$-alkoxycarbonyl, and/or may be substituted by groups of the formulae —$OSO_2$—$CH_3$ or $(CO)_a$—$NR^{17}R^{18}$, in which a represents a number 0 or 1, $R^{17}$ and $R^{18}$ are identical or different, and each represents hydrogen or aryl, aralkyl having 6 to 10 carbon atoms, or represents $(C_1-C_6)$-alkyl which is optionally substituted by $(C_1-C_6)$-alkoxycarbonyl, hydroxyl, phenyl or benzyl, where phenyl or benzyl are optionally mono- or polysubstituted by identical or different substituents from the group consisting of hydroxyl, carboxyl, $(C_1-C_6)$-alkyl and $(C_1-C_6)$-alkoxy, or $(C_1-C_6)$-alkyl is optionally substituted by groups of the formulae NH—CO—$CH_3$ or NH—CO—$CF_3$, or $R^{17}$ and $R^{18}$ together with the nitrogen atom form a morpholine, piperidinyl or pyrrolidinyl ring, or $R^3$ represents phenyl which is optionally substituted by methoxy, or $R^2$ and $R^3$ together form a radical of the formula

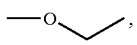

$R^4$ represents hydrogen, $(C_1-C_4)$-alkyl, $(C_2-C_4)$-alkenyl, benzoyl or represents acyl having 2 to 6 carbon atoms, $R^5$ represents pyridyl which is substituted up to 3 times by identical or different substituents from the group consisting of halogen, hydroxyl, cyano, trifluoromethyl, $(C_1-C_6)$-alkoxy, $(C_1-C_6)$-alkyl, $(C_1-C_6)$-alkylthio, carbalkoxy, $(C_1-C_6)$-acyloxy, amino, nitro, mono- and $(C_1-C_6)$-dialkylamino, and salts thereof.

In the context of the invention, cycloalkyl having 3 to 6 carbon atoms or $(C_3-C_6)$-cycloalkyl represents cyclopropyl, cyclopentyl, cyclobutyl or cyclohexyl. Preference is given to cyclopentyl or cyclohexyl.

Aryl generally represents an aromatic radical having 6 to 10 carbon atoms. Preferred aryl radicals are phenyl and naphthyl.

In the context of the invention, $(C_1-C_6)$-acyl represents a straight-chain or branched acyl radical having 1 to 6 carbon atoms. Preference is given to a straight-chain or branched acyl radical having 1 to 4 carbon atoms. Particularly preferred acyl radicals are acetyl and propionyl.

In the context of the invention, $(C_1-C_6)$-alkyl represents a straight-chain or branched alkyl radical having 1 to 6 carbon atoms. Examples which may be mentioned are: methyl, ethyl, propyl, isopropyl, tert-butyl, n-pentyl and n-hexyl.

Preference is given to a straight-chain or branched alkyl radical having 1 to 4 carbon atoms.

In the context of the invention, $(C_2-C_6)$-alkenyl represents a straight-chain or branched alkenyl radical having 2 to 5 carbon atoms. Preference is given to a straight-chain or branched alkenyl radical having 3 to 5 carbon atoms. Examples which may be mentioned are: ethenyl, propenyl, alkyl, n-pentenyl and n-hexenyl.

In the context of the invention, $(C_1-C_6)$-alkoxy represents a straight-chain or branched alkoxy radical having 1 to 6 carbon atoms. Preference is given to a straight-chain or branched alkoxy radical having 1 to 4 carbon atoms. Examples which may be mentioned are: methoxy, ethoxy and propoxy.

In the context of the invention, $(C_1-C_6)$-alkylthio represents a straight-chain or branched alkylthio radical having 1 to 6 carbon atoms. Preference is given to a straight-chain or branched alkylthio radical having 1 to 4 carbon atoms. Examples which may be mentioned are: methylthio, ethylthio and propylthio.

In the context of the invention, $(C_1-C_6)$-alkoxycarbonyl represents a straight-chain or branched alkoxycarbonyl radical having 1 to 6 carbon atoms. Preference is given to a straight-chain or branched alkoxycarbonyl radical having 1 to 4 carbon atoms. Examples which may be mentioned are: methoxycarbonyl, ethoxycarbonyl and propoxycarbonyl.

A straight-chain, branched or cyclic, saturated or unsaturated $(C_1-C_8)$-hydrocarbon radical includes, for example, the above-described $(C_1-C_6)$-alkyl, $(C_2-C_6)$-alkenyl or $(C_3-C_6)$-cycloalkyl, preferably $(C_1-C_6)$-alkyl.

The compounds according to the invention may exist in stereoisomeric forms which are related either as image and mirror image (enantiomers), or which are not related as image and mirror image (diastereomers). The invention relates both to the enantiomers or diastereomers and to their respective mixtures. The racemic forms can, just like the diastereomers, be separated in a known manner into the stereoisomerically pure constituents.

The compounds of the present invention include the isomers of the general formulae (I) and (Ia) and mixtures thereof. If $R^4$ is hydrogen, the isomers (I) and (Ia) exist in a tautomeric equilibrium:

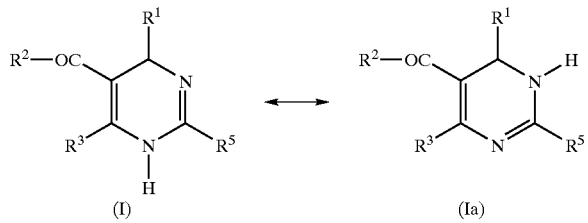

(I)            (Ia)

The substances according to the invention may also be present as salts. In the context of the invention, preference is given to physiologically acceptable salts.

Physiologically acceptable salts can be salts of the compounds according to the invention with inorganic or organic acids. Preference is given to salts with inorganic acids, such as, for example, hydrochloric acid, hydrobromoic acid, phosphoric acid or sulphuric acid, or to salts with organic carboxylic or sulphonic acids, such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluene-sulphonic acid or naphthalenedisulphonic acid.

Physiologically acceptable salts can also be metal or ammonium salts of the compounds according to the invention. Particular preference is given to, for example, sodium, potassium, magnesium or calcium salts, and also to ammonium salts which are derived from ammonia, or organic amines, such as, for example, ethylamine, di- or triethylamine, di- or triethanolamine, dicyclohexylamine, dimethylarninoethanol, arginine, lysine, ethylenediamine or 2-phenylethylamine.

Preference is given to compounds of the general formulae (I) and (Ia) according to the invention in which $R^1$ represents phenyl, furyl, thienyl, pyridyl, cyclopentyl or cyclohexyl or represents radicals of the formulae

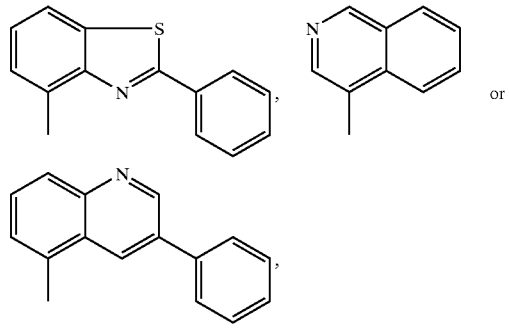

where the abovementioned ring systems are optionally mono- or disubstituted by identical or different substituents selected from the group consisting of halogen, trifluoromethyl, nitro, $SO_2$—$CF_3$, methyl, cyano, trifluoromethoxy, amino, hydroxyl, carboxyl, methoxycarbonyl and radicals of the formulae —CO—NH—$CH_2$—$C(CH_3)_3$, —CO—NH($CH_2)_2$OH, —CO—NH—$CH_2$—$C_6H_5$, —CO—NH—$C_6H_5$, —CO—NH—(pOH)—$C_6H_4$, —O—$CH_2$—$C_6H_5$ or —S—pCl—$C_6H_4$, $R^2$ represents a radical of the formula $-XR^{12}$ or $-NR^{13}R^{14}$, in which
   X represents a bond or an oxygen atom,
   $R^{12}$ represents hydrogen, ($C_1$–$C_4$)-alkenyl, ($C_1$–$C_4$)-alkoxycarbonyl or ($C_1$–$C_4$)-alkyl which are optionally substituted by pyridyl, cyano, phenoxy, benzyl or by a radical of the formula $-NR^{15}R^{16}$, in which
      $R^{13}$ and $R^{16}$ are identical or different, and each represents hydrogen, benzyl or ($C_1$–$C_4$)-alkyl,
   $R^{13}$ and $R^{14}$ are identical or different, and each represents hydrogen, ($C_1$–$C_4$)-alkyl or cyclopropyl,
$R^3$ represents hydrogen, amino or a radical of the formula

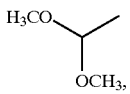

or represents formyl, cyano, trifluoromethyl, cyclopropyl or pyridyl, or represents ($C_1$–$C_4$)-alkyl which is optionally substituted by halogen, ($C_1$–$C_4$)-alkoxycarbonyl, hydroxyl or by triazolyl, which for its part may be substituted up to 3 times by ($C_1$–$C_4$)-alkoxycarbonyl, and/or alkyl is optionally substituted by groups of the formulae $-OSO_2-CH_3$ or $(CO)_a-NR^{17}R^{18}$, in which
   a represents a number 0 or 1,
   $R^{17}$ and $R^{18}$ are identical or different, and each represents hydrogen, phenyl or benzyl, or represents $C_1$–$C_4$-alkyl which is optionally substituted by ($C_1$–$C_4$)-alkoxycarbonyl, hydroxyl, phenyl or benzyl, where phenyl or benzyl are optionally mono- or polysubstituted by identical or different substituents from the group consisting of hydroxyl, carboxyl, ($C_1$–$C_4$)-alkyl and ($C_1$–$C_4$)-alkoxy, and/or ($C_1$–$C_4$)-alkyl is optionally substituted by radicals of the formulae $-NH-CO-CH_3$ or $-NH-CO-CF_3$, or
   $R^{17}$ and $R^{18}$ together with the nitrogen atom form a morpholine, piperidinyl or pyrrolidinyl ring, or
$R^3$ represents phenyl which is optionally substituted by methoxy, or
$R^2$ and $R^3$ together form a radical of the formula

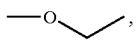

$R^4$ represents hydrogen, methyl, benzoyl or acetyl,
$R^5$ represents pyridyl which is substituted up to 2 times by identical or different substituents from the group consisting of fluorine, chlorine, bromoine, ($C_1$–$C_4$)-alkoxy and ($C_1$–$C_4$)-alkyl,
and salts thereof.

Particular preference is given to compounds of the general formulae (I) and (Ia) according to the invention, in which
$R^1$ represents phenyl, furyl, thienyl, pyridyl, cyclopentyl, cyclohexyl or represents radicals of the formulae

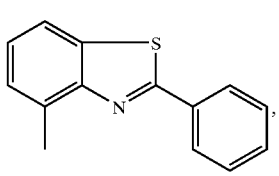 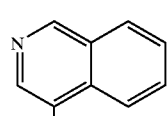 or

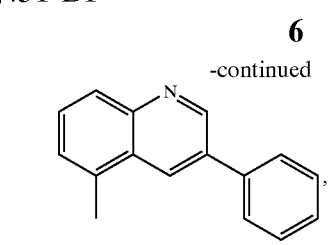

where the abovementioned ring systems are optionally substituted up to 2 times by identical or different substituents selected from the group consisting of fluorine, chlorine, bromine, iodine, hydroxyl, trifluoromethyl, nitro, $SO_2-CF_3$, methyl, cyano, amino, trifluoromethoxy, carboxyl, methoxycarbonyl and radicals of the formulae $-CO-NH-CH_2-C(CH_3)_3$, $-CO-NH(CH_2)_2OH$, $-CO-NH-CH_2-C_6H_5$, $-CO-NH-C_6H_5$, $-CO-NH-(pOH)-C_6H_4$, $-O-CH_2-C_6H_5$ or $-S-pCl-C_6H_4$,
$R^2$ represents a radical of the formula $-XR^{12}$ or $-NR^{13}R^{14}$, in which
   X represents a bond or an oxygen atom,
   $R^{12}$ represents hydrogen, ($C_1$–$C_3$)-alkenyl, ($C_1$—$C$,)-alkoxycarbonyl or ($C_1$–$C_4$)-alkyl which are optionally substituted by pyridyl, cyano, phenoxy, benzyl or by a radical of the formula $-NR^{15}R^{16}$, in which
      $R^{15}$ and $R^{16}$ are identical or different, and each represents hydrogen or methyl,
   $R^{13}$ and $R^{14}$ are identical or different, and each represents hydrogen, ($C_1$–$C_3$)-alkyl or cyclopropyl,
$R^3$ represents hydrogen, amino or represents a radical of the formula

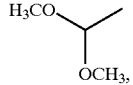

represents formyl, cyano, trifluoromethyl, cyclopropyl or pyridyl, or
represents ($C_1$–$C$,)-alkyl which is optionally substituted by fluorine, chlorine, ($C_1$–$C_3$)-alkoxycarbonyl, hydroxyl or by triazolyl, which for its part may be substituted up to 3 times by ($C_1$–$C_3$)-alkoxycarbonyl, and/or alkyl is optionally substituted by groups of the formulae $-OSO_2-CH_3$ or $(CO)_a-NR^{17}R^{18}$, in which
   a represents a number 0 or 1,
   $R^{17}$ and $R^{18}$ are identical or different, and each represents hydrogen, phenyl or benzyl, or represents ($C_1$–$C_3$)-alkyl which is optionally substituted by ($C_1$–$C_3$)-alkoxycarbonyl, hydroxyl, phenyl or benzyl, where phenyl or benzyl are optionally mono- or disubstituted by identical or different substituents from the group consisting of hydroxyl, carboxyl, ($C_1$–$C_3$)-alkyl and ($C_1$–$C_3$)-alkoxy, and/or ($C_1$–$C_4$)-alkyl is optionally substituted by radicals of the formulae $-NH-CO-CH_3$ or $-NH-CO-CF_3$, or
   $R^{17}$ and $R^{18}$ together with the nitrogen atom form a morpholine, piperidinyl or pyrrolidinyl ring, or
$R^3$ represents phenyl which is optionally substituted by methoxy, or
$R^2$ and $R^3$ together form a radical of the formula

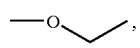

$R^4$ represents hydrogen, methyl, benzoyl or acetyl,

R[5] represents pyridyl which is substituted up to 2 times by identical or different substituents from the group consisting of fluorine, chlorine, (C[1]–C[3])-alkoxy and (C[1]–C[3])-alkyl,
and salts thereof.

Very particular preference is given to compounds of the general formulae (I) and (Ia) according to the invention, in which R[1] represents phenyl which is optionally substituted up to 2 times by identical or different substituents from the group consisting of fluorine, chlorine, bromine, iodine, methyl and nitro, R[2] represents —XR[12] in which X represents oxygen and R[12] represents straight-chain or branched alkyl having up to 4 carbon atoms, R[3] represents methyl, ethyl or cyclopropyl, or R[2] and R[3] together form a radical of the formula

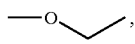

R[4] represents hydrogen or acetyl, and

R[5] represents pyridyl which is substituted up to two times by identical or different substituents from the group consisting of fluorine and chlorine,
and salts thereof.

Even more preference is given to compounds of the general formula (I) or (Ia) according to the invention in which R[5] represents 2-pyridyl which can be substituted by 1 to 2 fluorine atoms.

Very particular preference is also given to those compounds of the general formulae (I) and (Ia) according to the invention which are listed in Table A:

TABLE A

Structure

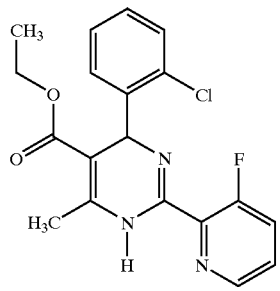

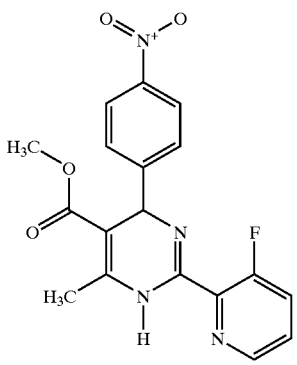

TABLE A-continued

Structure

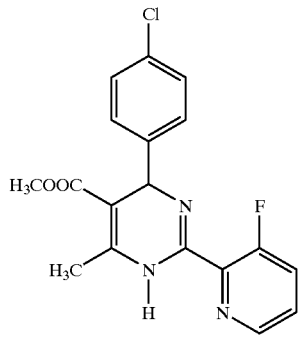

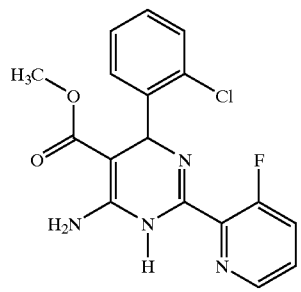

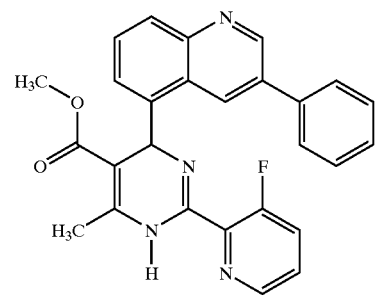

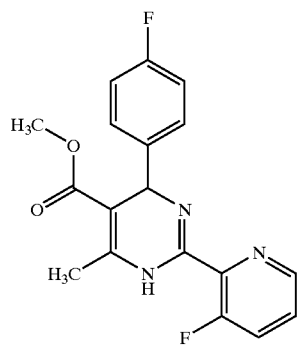

TABLE A-continued
Structure
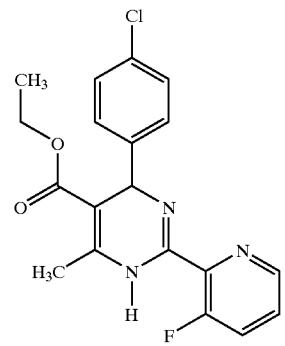
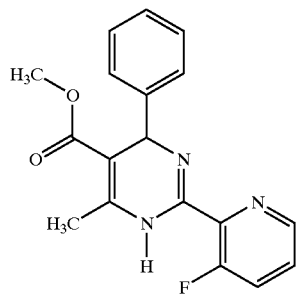
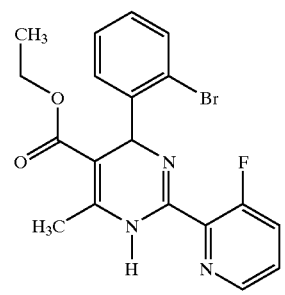
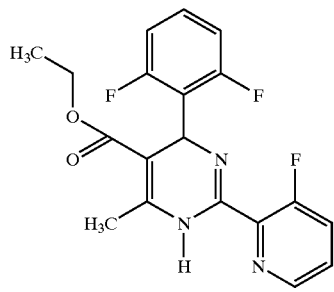
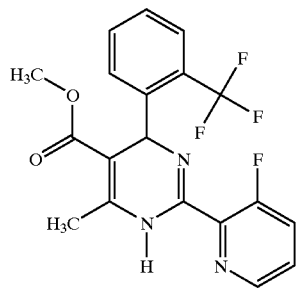
TABLE A-continued
Structure
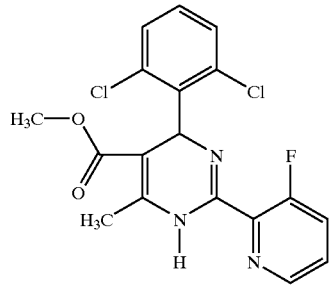
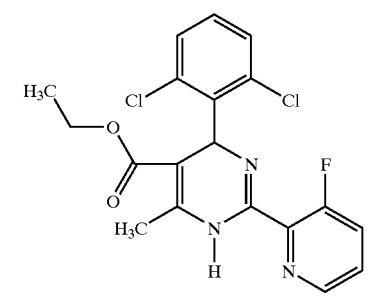
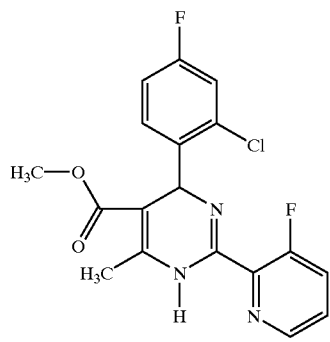
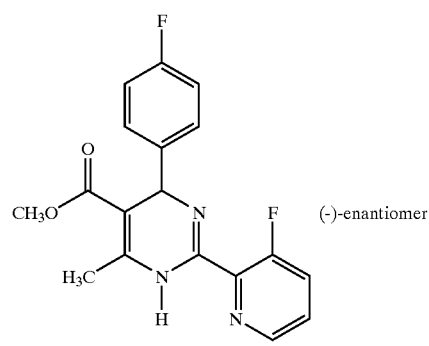
(-)-enantiomer TABLE A-continued
Structure
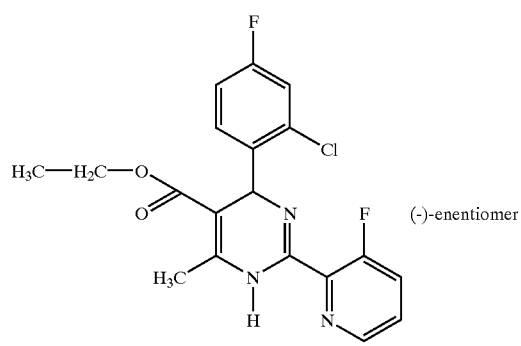
(−)-enentiomer
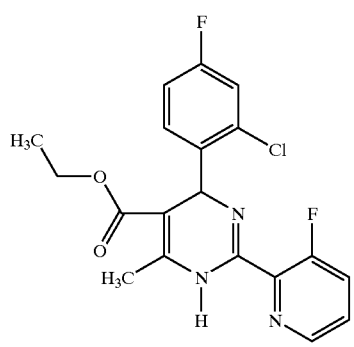
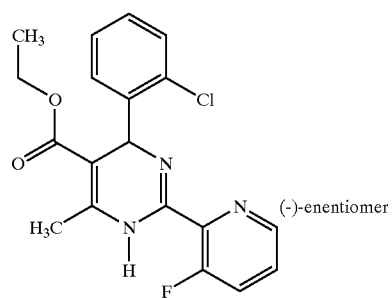
(−)-enentiomer
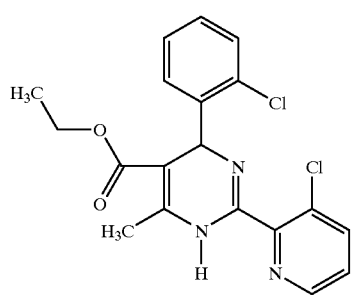
TABLE A-continued
Structure
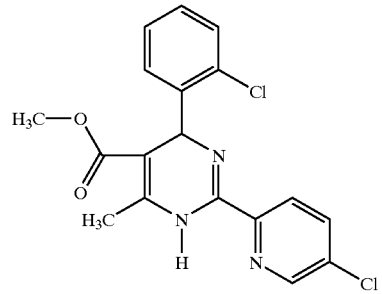
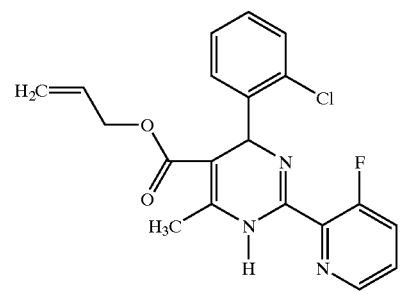
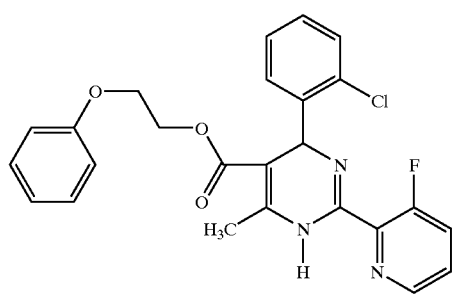
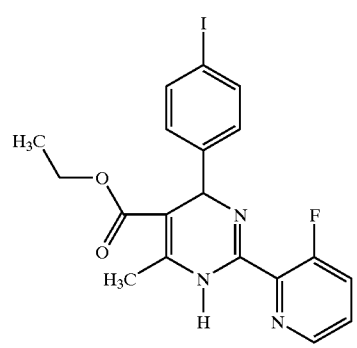
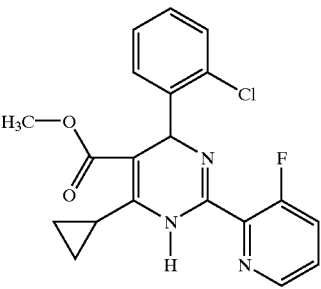

TABLE A-continued
Structure
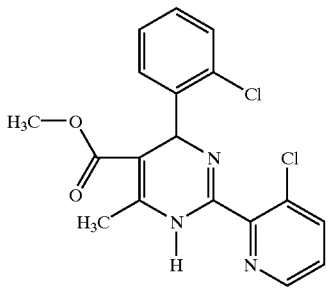
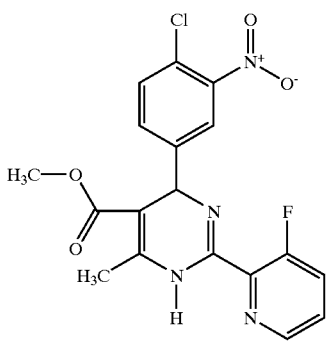
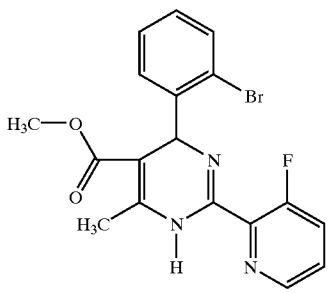
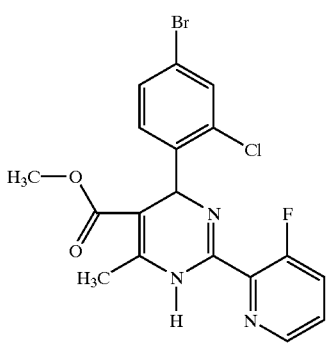
TABLE A-continued
Structure
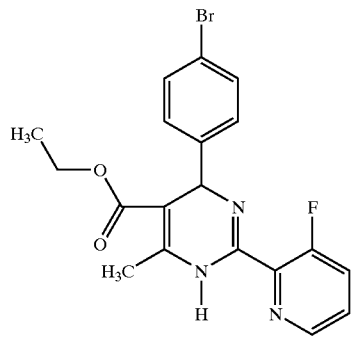
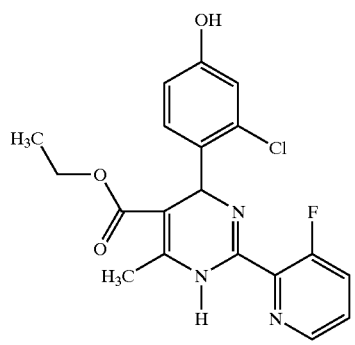
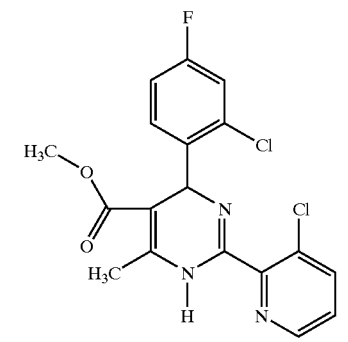
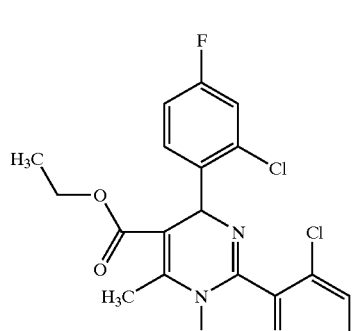

TABLE A-continued
Structure
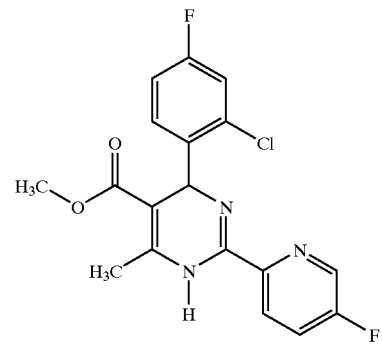
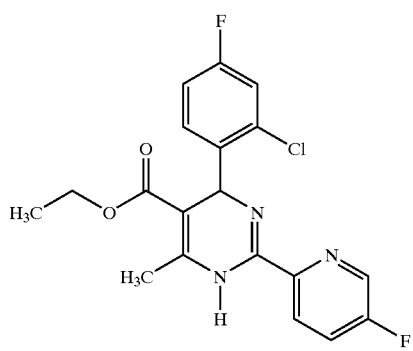
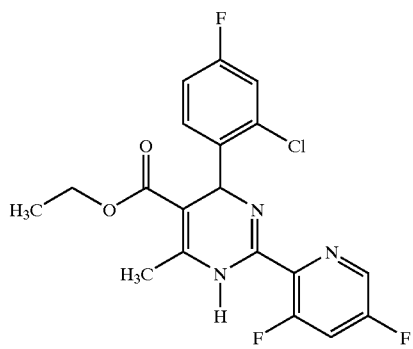
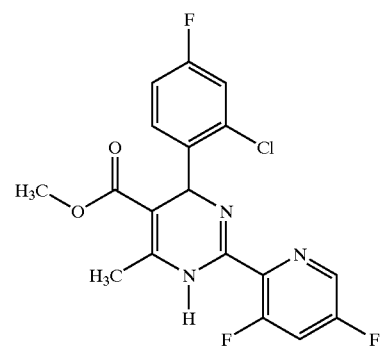
TABLE A-continued
Structure
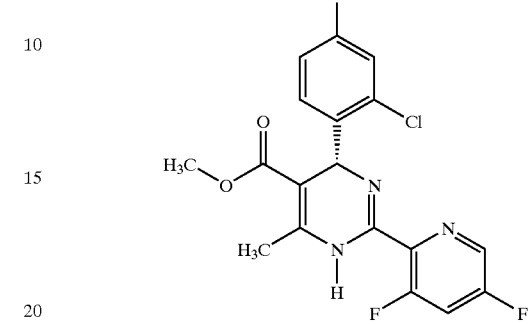
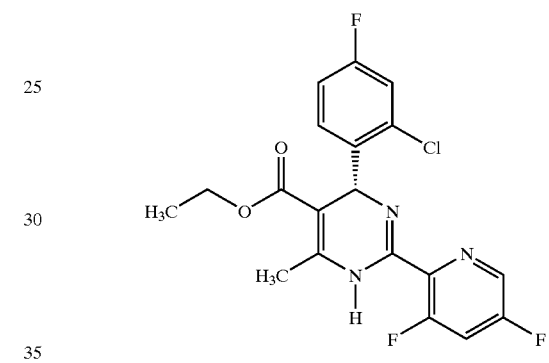
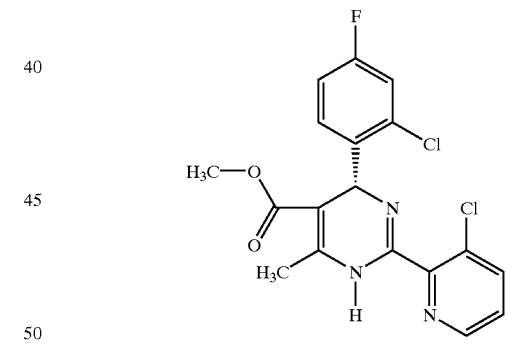
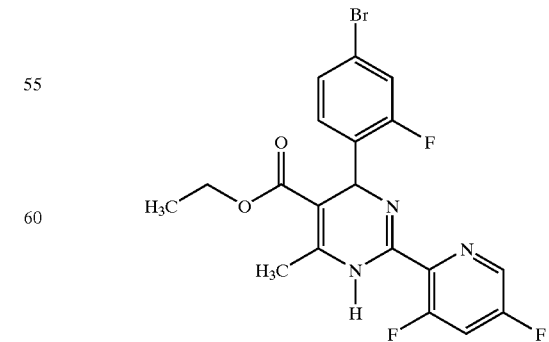

TABLE A-continued

Structure

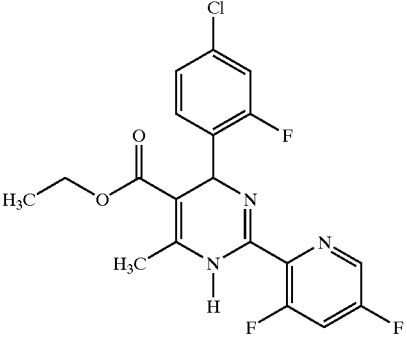

Very particular preference is given to the following compounds:

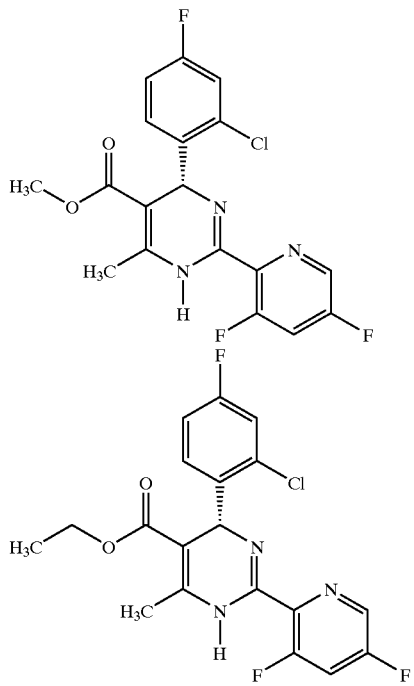

The compounds of the general formula (I) according to the invention can be prepared by
[A] reacting aldehydes of the general formula (II)

$R^1$—CHO　(II)

in which
  $R^1$ is as defined above,
  with amidines or their hydrochlorides of the formula (III)

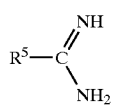
                                                                    (III)

in which
  $R^5$ is as defined above,
  and compounds of the general formula (IV)

$R^3$—CO—CH$_2$—CO—$R^2$　(IV)

in which
  $R^2$ and $R^3$ are each as defined above,
  if appropriate in the presence of inert organic solvents, with or without addition of base or acid, or
[B] reacting compounds of the general formula (V)

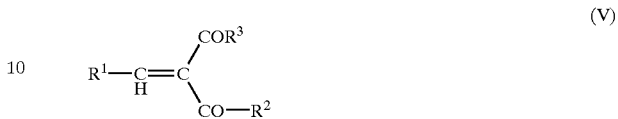
                                                                    (V)

in which
  $R^1$, $R^2$ and $R^3$ are each as defined above,
  with amidines of the general formula (III)

                                                                    (III)

in which
  $R^5$ is as defined above,
  if appropriate in the presence of inert organic solvents at temperatures between 20° C. and 150° C., with or without addition of base or acid, or
[C] reacting aldehydes of the general formula (II)

$R^1$—CHO　(II)

in which
  $R^1$ is as defined above,
  with compounds of the general formula (VI)

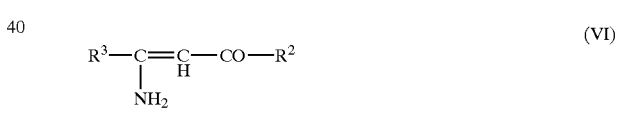
                                                                    (VI)

in which
  $R^2$ and $R^3$ are each as defined above,
  and amidines of the general formula (III) as described above, or
[D] reacting aldehydes of the general formula (II) with compounds of the general formula (IV) and imino ethers of the general formula (VII)

                                                                    (VII)

in which
  $R^5$ is as defined above, and
  $R^1$ represents $(C_1$–$C_4)$-alkyl,
  in the presence of ammonium salts.
The processes according to the invention can be illustrated using the following schemes as examples:

[A]

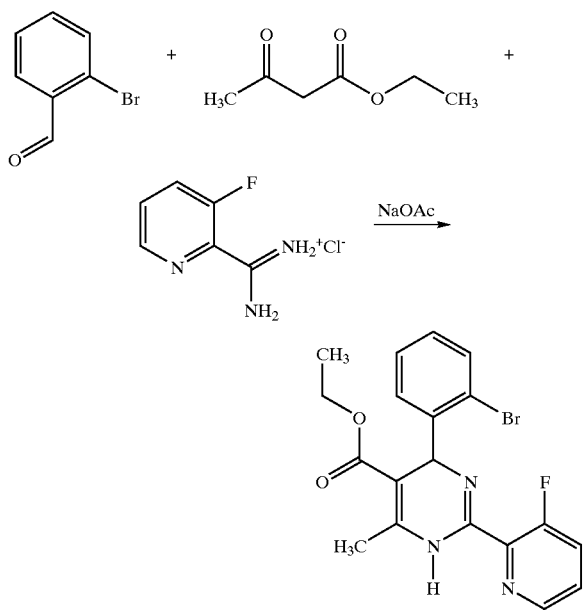

Solvents which are suitable for all process variants A, B, C and D are all inert organic solvents. These preferably include alcohols, such as ethanol, methanol, isopropanol, ethers, such as dioxane, diethyl ether, tetrahydrofuran, glycol monomethyl ether, glycol dimethyl ether or glacial acetic acid, dimethyl formamide, dimethyl sulphoxide, acetonitrile, pyridine and hexamethylphosphoric triamide.

The reaction temperatures can be varied within a relatively wide range. In general, the reaction is carried out between 20 and 150° C., but preferably at the boiling point of the solvent in question.

The reaction can be carried out at atmospheric pressure, or else at elevated pressure. In general, the reaction is carried out at atmospheric pressure.

The reaction can be carried out with or without addition of base or acid; however, it has been found that a reaction according to the invention is preferably carried out in the presence of relatively weak acids, such as, for example, acetic acid or formic acid.

The aldehydes of the general formula (II) used as starting materials are known or can be prepared by methods known from the literature (cf. T. D. Harris and G. P. Roth, J. Org. Chem. 44, 146 (1979), German Offenlegungsschrift 2 165 260, July 1972, German Offenlegungsschrift 2 401 665, July 1974, Mijano et al., Chem. Abstr. 59, (1963), 13 929 c, E. Adler and H.-D. Becker, Chem. Scand. 15, 849 (1961), E. P. Papadopoulos, M. Mardin and Ch. Issidoridis, J. Org. Chem. Soc. 78, 2543 (1956)).

The ylidene-β-keto esters of the formula (V) used as starting materials can be prepared by methods known from the literature [cf. G. Jones, "The Knoevenagel Condensation", in Organic Reactions, Vol. XV, 204 ff. (1967)].

The enaminocarboxylic esters of the formula (VI) and the imino ethers of the general formula (VII) used as starting materials are known or can be prepared by methods known from the literature [cf. S. A. Glickman and A. C. Cope, J. Am. Chem. Soc. 67, 1017 (1945)].

The β-ketocarboxylic esters of the general formula (IV) used as starting materials are known or can be prepared by methods known from the literature [for example D.

Borrmann, "Umsetzung von Diketen mit Alkoholen, Phenolen und Mercaptanen", in Houben-Weyl, Methoden der organischen Chemie, Vol. VII/4, 230 ff (1968); Y. Oikawa, K. Sugano and O. Yonemitsu, J. Org. Chem. 43, 2087 (1978)].

Some of the compounds of the general formula (III) are known, or, in the case where $R^5$ is difluorinated pyridyl, are novel, and they can be prepared by reacting compounds of the formula (VIII)

$$R^5—CN \qquad \text{(VIII)}$$

in which $R^5$ is as defined above, in the customary way via the imino ethers and finally with ammonium chloride in methanol [cf. in this context W. K. Fife, Heterocycles 22, 93–96 (1984); T. Sakamoto, S. Kaneda, S. Nishimura, H. Yamanaka, Chem. Pharm. Bull. 33, 565–571 (1986)] or other processes known from the literature, such as, for example, Garigipati, Tetrahedron Lett. 1990, pp. 1969–1972, Boere et al., J. Organomet. Chem. 1987, 331, 161, Caton et al., J. Chem. Soc. 1967, 1204.

All process steps are carried out at atmospheric pressure and in a temperature range of from 0° C. to 130° C., preferably from 20° C. to 100° C.

Thus, the invention also relates to an intermediate of the formula below

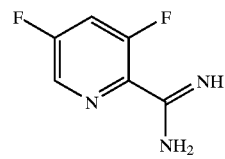

and its salts from which preferred end products can be prepared. With respect to the salts of this compound, reference is made to the abovementioned acid addition salts and in particular to the hydrochloride. This compound is prepared as described in the examples, and, in this respect, reference is also made to the reaction scheme shown below.

The compounds of the formula (VIII) are known per se or can be prepared by known processes similarly to Example I and II by reacting pyridines of the general formula (IX)

$$R^5—H \qquad \text{(IX)}$$

in which the hydrogen is ortho to the nitrogen and in which $R^5$ is as defined above, initially at from 50 to 150° C., preferably at 100° C., in $H_2O_2$/glacial acetic acid to give the corresponding N-oxides, followed by a reaction with trimethylsilyl cyanide (TMSCN) by processes known from the literature in the abovementioned inert solvents, preferably acetonitrile, THF, toluene at room temperature or at reflux temperature, if appropriate with addition of bases such as triethylamine or DBU, or by replacing, in compounds of the formula (X)

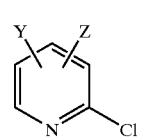

(X)

in which Y and Z represent the substitution radicals of the pyridyl ring mentioned under $R^5$, the chlorine with cyanide, using cyanides, such as potassium cyanide or copper cyanide, or by reacting, in the case where $R^5$ represents difluoropyridyl, compounds of the formula (XI)

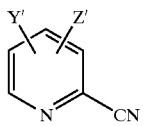
(XI)

in which Y' and Z' are identical or different, and each represents chlorine or bromine, with alkali metal or ammonium fluorides, preferably potassium fluoride, by processes known from the literature, in polar solvents, such as, for example, polyglycols and ethers thereof, DMSO or sulpholane, if appropriate with addition of phase-transfer catalysts, in a halogen-fluorine exchange reaction.

Thus, the invention also relates to a compound of the formula below from which the corresponding amidine intermediate can be prepared in the manner described in the examples:

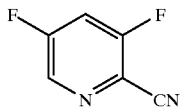

The above process is, with respect to the 3,5-difluoropyridyl compounds, illustrated in an exemplary manner by the following reaction scheme:

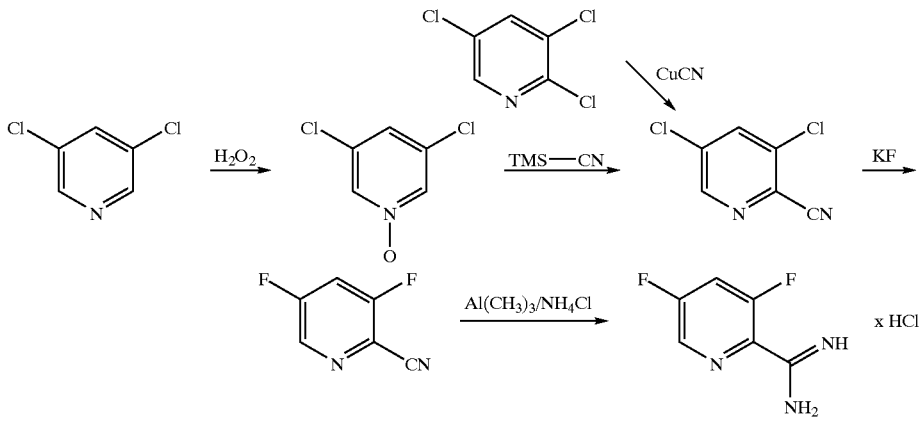

The antiviral activity of the compounds according to the invention was investigated following the methods described by Sells et al. (M. A. Sells, M.-L. Chen, and G. Acs (1987) Proc. Natl. Acad. Sci. 84, 1005–1009) and Korba et al. (B. E. Korba and J. L. Gerin (1992) Antiviral Research 19, 55–70).

The antiviral tests were carried out in 96-well microtitre plates. Only growth medium and HepG2.2.15 cells were added to the first vertical row of the plate. This row served as virus control.

Stock solutions of the test compounds (50 mM) were initially dissolved in DMSO, and further dilutions were prepared in the growth medium of HepG2.2.15. The compounds according to the invention, usually in a test concentration of 100 µM (1st test concentration), were in each case pipetted into the second vertical test row of the microtitre plate and subsequently diluted, by a factor of 2 each time, up to $2^{10}$-fold, using growth medium plus 2% of foetal calf serum (volume 25 µl).

225 µl of a HepG2.2.15 cell suspension ($5 \times 10^4$ cells/ml) in growth medium plus 2% foetal calf serum were then added to each well of the microtitre plate.

The test batch was incubated at 37° C., 5% $CO_2$, for 4 days.

The supernatant was subsequently siphoned off and discarded, and 225 µl of freshly prepared growth medium were added to the wells. Once more, the compounds according to the invention were added, in each case as a solution 10-fold-concentrated, in a volume of 25 µl. The batches were incubated for another 4 days.

Before the supernatants were harvested for determining the antiviral effect, the HepG2.2.15 cells were examined under the light microscope or by biochemical detection methods (for example Alamar Blue staining or Trypan Blue staining) for cytotoxic changes.

The supernatants were subsequently harvested and, by means of reduced pressure, siphoned onto 96-well dot blot chambers covered with a nylon membane (in accordance with the specifications of the manufacturer).

Determination of the Cytotoxicity

Substance-induced cytotoxic or cytostatic changes in the HepG2.2.15 cells were determined as changes in the cell morphology, for example under a light microscope. Such substance-induced changes of the HepG2.2.15 cells in comparison with untreated cells could be observed, for example, as cell lysis, vacuolization or changed cell morphology. 50% cytotoxicity (Tox.-50) means that 50% of the cells have a morphology which is similar to the corresponding cell control.

The compatibility of some of the compounds according to the invention was additionally tested on other host cells, such as, for example, HeLa cells, primary peripheral human blood cells or transformed cell lines, such as H-9 cells. At concentrations of the compounds according to the invention of >10 µM, no cytotoxic changes were observed.

Determination of the Antiviral Activity

After transfer of the supernatants onto the nylon membrane of the blot apparatus (see above), the supernatants of the HepG2.2.15 cells were denatured (1.5 M NaCl/0.5 N NaOH), neutralized (3 M NaCl/0.5 M Tris HCl, pH 7.5) and washed (2×SSC). By incubation of the filters at 120° C. for 2–4 hours, the DNA was subsequently baked onto the membrane.

Hybridization of the DNA

The viral DNA of the treated HepG2.2.15 cells on the nylon filters was usually detected using non-radioactive digoxygenin-labelled hepatitis B-specific DNA probes which were in each case in accordance with the specifications of the manufacturer labelled with digoxygenin, purified and used for hybridization.

The prehybridization and hybridization was carried out in 5×SSC, 1×blocking reagent, 0.1% N-lauroylsarcosine, 0.02% SDS and 100 μg of DNA from herring sperm. The prehybridization was carried out at 60° C. for 30 minutes and the specific hybridization was carried out using 20 to 40 ng/ml of the digoxygenated denatured HBV-specific DNA (14 hours, 60° C.). The filters were subsequently washed.

Determination of HBV DNA by Digoxygenin Antibodies

The digoxygenin-labelled DNA was detected immunologically in accordance with the specifications of the manufacturer:

The filters were washed and prehybridized in a blocking agent (in accordance with the specifications of the manufacturer). They were subsequently hybridized for 30 minutes using an anti-DIG antibody linked to alkaline phosphatase. After a washing step, the substrate of alkaline phosphatase, CSPD, was added, incubated with the filters for 5 minutes, subsequently wrapped in plastic film and incubated at 37° C. for a further 15 minutes. The chemiluminescence of the Hepatitis B-specific DNA signals was visualized by exposition of the filters on an X-ray film (incubation, depending on the signal strength: 10 minutes to 2 hours).

The half-maximum inhibitory concentration (IC-50, inhibitory concentration 50%) was determined as the concentration at which the hepatitis B-specific band was reduced by 50% in comparison with an untreated sample by the compound according to the invention.

Surprisingly, the treatment of the hepatitis B virus-producing HepG2.2.15 cells with the compounds according to the invention resulted in a reduction of viral DNA in the cell culture supernatant, the viral DNA being released by the cells into the cell culture supernatant in the form of virions.

The compounds according to the invention have a novel unforeseeable and useful action against viruses. Surprisingly, they are antivirally active against hepatitis B (HBV) and are therefore suitable for treating virus-induced diseases, in particular acute and chronically persisting HBV virus infections. A chronic viral disease caused by HBV can lead to clinical pictures of various gravity; as is known, chronic hepatitis B virus infection frequently results in cirrhosis of the liver and/or hepatocellular carcinoma.

Examples which may be mentioned of areas of indication for the compounds usable according to the invention are:

The treatment of acute and chronic virus infections which may lead to an infectious hepatitis, for example infections with hepatitis B viruses. Particular preference is given to the treatment of chronic hepatitis B infections and the treatment of acute hepatitis B virus infection.

The present invention encompasses pharmaceutical formulations which, in addition to non-toxic inert pharmaceutically acceptable excipients, contain one or more compounds of the formulae (I), (Ia) or of Table A or which comprise one or more active compounds of the formulae (I), (Ia) and (Ib), and also encompasses processes for producing these formulations.

In the abovementioned pharmaceutical formulations, the active compounds of the formulae (I), (Ia) and (Ib) should be present in a concentration of approximately 0.1–99.5% by weight, preferably of approximately 0.5–95% by weight of the total mixture.

The abovementioned pharmaceutical formulations may, in addition to the compounds of the formulae (I), (Ia) and (Ib), also contain further pharmaceutically active compounds.

The abovementioned pharmaceutical formulations are produced in a customary manner by known methods, for example by mixing the active compound(s) with the excipient(s).

In general, it has been found to be advantageous both in human and veterinary medicine to administer the active compound(s) in total amounts of from approximately 0.5 to approximately 500, preferably 1–100 mg/kg of body weight per 24 hours, if appropriate in the form of several individual doses, to obtain the desired results. An individual dose preferably contains the active compound(s) in amounts of from approximately 1 to approximately 80, in particular 1–30 mg/kg of body weight. However, it may be necessary to deviate from the specified dosages, depending on the nature and the body weight of the object to be treated, the nature and the severity of the disease, the formulation type and the administration of the medicament, and the time or interval within which administration is carried out.

STARTING MATERIALS

EXAMPLE I

3-Fluoropyridine N-oxide

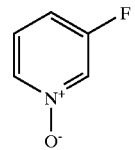

11.10 g (114.324 mmol) of 3-fluoropyridine are dissolved in 74.00 ml of acetic acid. 22.20 ml of $H_2O_2$ are added, and the mixture is stirred at a bath temperature of 100° C. for 7 hours. The mixture is then concentrated to 30 ml, 30 ml of water are added and the mixture is once more concentrated to 30 ml. The solution is stirred with dichloromethane, made alkaline by addition of $K_2CO_3$, the phases are separated and the aqueous phase is extracted twice with dichloromethane, dried and concentrated.

Yield: 11.5 g (88.9%); m.p.: 66–68° C.

EXAMPLE II

2-Cyano-3-fluoropyridine

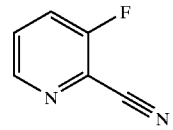

5.20 g (45.980 mmol) of the compound from Example I are dissolved in 50 ml of acetonitrile. Under argon, 13.70 g (138.092 mmol) of trimethylsilylnitrile are added, and 12.80 ml of triethylamine are slowly admixed. The solution is stirred under reflux for 7 hours and then at room temperature overnight. The solution is then concentrated using a water pump, taken up in dichloromethane, shaken 2× with 50 ml of 2N sodium carbonate, washed with water, dried and concentrated.

Yield (crude): 5.3 g (oil);

Column chromatography: methylene chloride to methylene chloride/ethyl acetate 10:1.

The oil solidifies!

EXAMPLE III

2-Amidino-3-fluoropyridine Hydrochloride

10.30 g (84.355 mmol) of the compound from Example II are dissolved in 30 ml of methanol. The solution is admixed with a solution of 0.40 g (17.391 mmol) of sodium in 65 ml of methanol and stirred at 20° C. for 72 hours. 5.44 g (101.682 mmol) of ammonium chloride (ground in a mortar) and 17.39 mmol (1.04 ml) of acetic acid are added and the mixture is stirred at 40° C. for 28 hours and cooled. Insoluble salt is filtered off with suction (1.78 g) and the filtrate is concentrated, concentrated with acetone and subsequently stirred with acetone, filtered off with suction and washed.

Yield: 10.6 g; m.p.:≈150° C. decomp.

EXAMPLE IV

2-Cyano-3,5-dichloro-pyridine

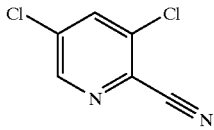

Method 1:

26 g (0.158 mol) of 3,5-dichloro-pyridine 1-oxide (Johnson et al., J. Chem. Soc. B, 1967, 1211) are dissolved in 80 ml of $CH_2Cl_2$ and admixed successively with 21.8 ml (0.174 mol) of trimethylsilyl cyanide and 14.6 ml (0.158 mol) of dimethylcarbamoyl chloride and stirred at room temperature for 48 h. The mixture is admixed with 100 ml of a 10% strength $NaHCO_3$ solution and stirred vigorously for 10 min. The phases are separated, the aqueous phase is extracted once with $CH_2Cl_2$ and the combined organic phases are dried and concentrated. The residue is chromatographed over silica gel using $CH_2Cl_2$ and recrystallized from a little methanol. This gives 11 g (40.2%) of 2-cyano-3,5-dichloro-pyridine (m.p.: 102° C.).

Method 2:

By the method of Troschuetz, R. et al., J. Heterocycl. Chem. 1996, 33, 1815–1821, 150 ml of diethylene glycol dimethyl ether (diglyme), 47.68 g (0.261 mol) of 2,3,5-trichloropyridine, 2.0 g (0.005 mol) of tetraphenylphosphonium bromide, 4.0 g (0.024 mol) of finely powdered potassium iodide and 75.0 g (0.838 mol) of copper(I) cyanide are added under nitrogen, and the mixture is stirred at reflux for 24 hours. Another 100 ml of diglyme, 2.0 g (0.005 mol) of tetraphenylphosphonium bromide, 4.0 g (0.024 mol) of finely powdered KI and 75 g (0.838 mol) of CuCN are subsequently added, and the mixture is stirred at reflux for a further 89 hours. The mixture is cooled to room temperature and filtered off with suction, and the filtrate is freed distillatively from most of the diglyme. The residue is taken up in toluene and washed with an aqueous solution of Mohr's salt and then with $NaHCO_3$ solution (peroxide test). The mixture is then washed free of diglyme using water and filtered through Celite, the filtrate is dried over $MgSO_4$ and the solution is concentrated. This gives 18.0 g (40.0%) of 2-cyano-3,5-dichloropyridine.

EXAMPLE V 3,5-Difluoro-pyridine-2-carbonitrile

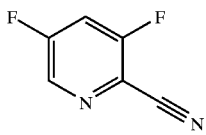

50 g (0.29 mol) of 3,5-dichloropyridine-2-carbonitrile (Example IV), 33.6 g (0.58 mol) of potassium fluoride and 10 g of polyethylene glycol 8000 are admixed with 125 ml of DMSO and heated at 160° C. for 30 min. After cooling, the product, together with the DMSO, is distilled off under high vacuum, and the distillate is poured into water, extracted with toluene and dried over $Na_2SO_4$. The product is reacted further as a solution in toluene.

($R_f$ value: 0.43, cyclohexane/ethyl acetate=7.3)

EXAMPLE VI 3,5-Difluoro-2-pyridinecarboximidamide Hydrochloride

33.4 g (0.624 mol) of ammonium chloride are suspended in 1 l of toluene and cooled to 0–5° C. 328 ml of trimethylaluminium (2 M in hexane, 0.624 mol) are added dropwise, and the mixture is stirred at RT until the evolution of methane has ceased. The solution of 3,5-dichloro-pyridine-2-carbonitrile in toluene (solution from Example V) is then added dropwise, and the mixture is then stirred at 80° C. overnight. After cooling to from 0 to −5° C., MeOH is added dropwise until the evolution of gas has ceased, the salts are filtered off with suction and washed to 2× with a little MeOH. The mixture is concentrated using a rotary evaporator and the residue is dissolved in 500 ml of $CH_2Cl_2$/MeOH (9:1) and once more filtered off with suction from inorganic salts. The mixture is concentrated using a rotary evaporator, giving 23.6 g (39.1%) of 3,5-difluoro-2-pyridinecarboximidamide as hydrochloride (m.p.: 183° C.).

$^1$H-NMR (DMSO-D6): 8.3–8.45(m, 1H), 8.8 (d, J=2 Hz, 1H), 9.7 (s, broad, 4H) ppm.

EXAMPLE VII

Methyl 2-Acetyl-3-(2-chloro-4-fluorophenyl)-2-propenoate

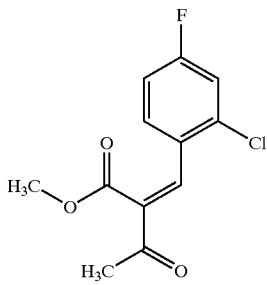

50 g (315 mmol) of 2-chloro-4-fluoro-benzaldehyde and 36.6 g (315 mmol) of methyl acetoacetate are dissolved in 150 ml of isopropanol and admixed with 1.7 ml of piperadine acetate. The mixture is stirred at room temperature overnight and then diluted with methylene chloride and extracted with water, dried over sodium sulphate and concentrated. The crude product is reacted further, as cis-trans mixture.

PREPARATION EXAMPLES
EXAMPLE 1

Ethyl 4-(2-Bromophenyl)-2-(3-fluoropyridin-2-yl)-6-methyl-1,4-dihydro-pyrimidin-5-carboxylate

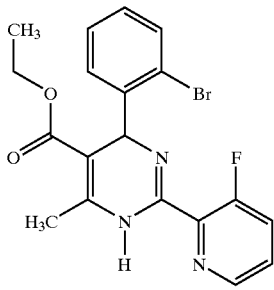

92.50 mg (500 μmol) of 2-bromobenzaldehyde in 3.00 ml of ethanol are admixed successively with 65.0 mg of ethyl acetoacetate, 91.80 mg of the compound from Example III and 43.06 mg of sodium acetate, and the mixture is boiled for 6 hours. The mixture is cooled, concentrated, dissolved in 2 ml of 1N HCl and 4 ml of H$_2$O and ethyl acetate, the phases are separated, the organic phase is extracted with 1 ml of 1 N HCl and water and the combined aqueous phases are washed with ether. The aqueous phase is made alkaline using dilute ammonia solution, extracted with ethyl acetate, and the organic phase is washed with H$_2$O, dried and concentrated. The residue is dissolved in a little ether and crystallized. The crystals are filtered off with suction, washed with ether and dried at 60° C. under reduced pressure.

TLC: pure (toluene/ethyl acetate=4:1);
Yield: 92 mg (44%);
m.p.: 163–165° C.

The compounds listed in Table 1 are prepared by the method of Example 1:

TABLE 1

| Example No.: | Structure | m.p. [° C.] | R$_f$ |
|---|---|---|---|
| 2 | 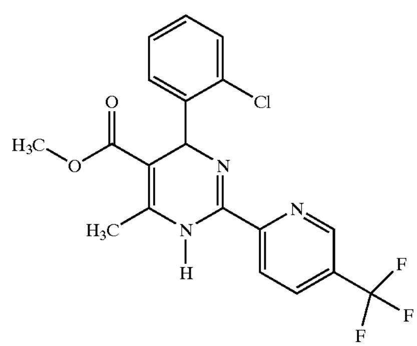 | 121–123 | — |
| 3 | 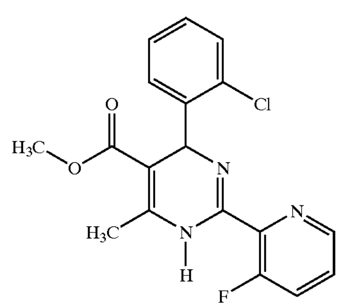 | >120 | — |

TABLE 1-continued

| Example No.: | Structure | m.p. [° C.] | R$_f$ |
|---|---|---|---|
| 4 | (ethyl 4-(2-chlorophenyl)-2-(3-fluoropyridin-2-yl)-6-methyl-1,4-dihydropyrimidine-5-carboxylate) | 152–53 | — |
| 5 | (methyl 2-(3-fluoropyridin-2-yl)-6-methyl-4-(4-nitrophenyl)-1,4-dihydropyrimidine-5-carboxylate) | 142–143 | — |
| 6 | (methyl 4-(2-chlorophenyl)-6-methyl-2-(6-methylpyridin-2-yl)-1,4-dihydropyrimidine-5-carboxylate) | 142–143 | — |
| 7 | (methyl 4-(4-chlorophenyl)-2-(3-fluoropyridin-2-yl)-6-methyl-1,4-dihydropyrimidine-5-carboxylate) | 139–140 | — |

TABLE 1-continued

| Example No.: | Structure | m.p. [° C.] | R_f |
|---|---|---|---|
| 8 | 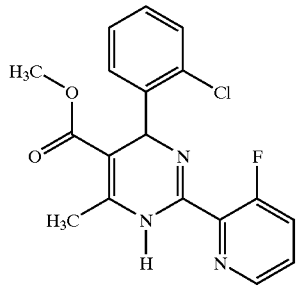 | 173–175 | — |
| 9 | 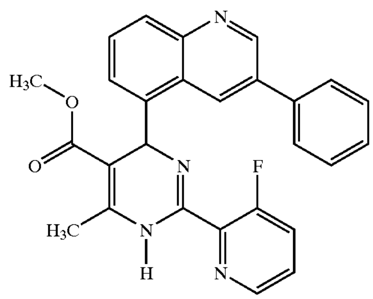 | 174–175 | — |
| 10 | 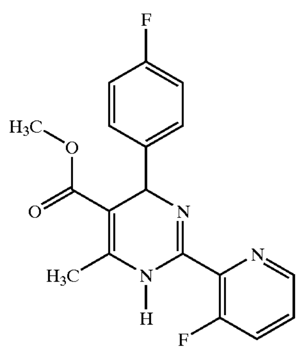 | 127–129 | — |
| 11 | 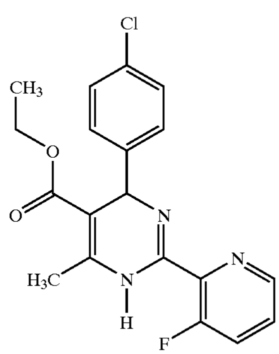 | 133–134 | — |

TABLE 1-continued

| Example No.: | Structure | m.p. [° C.] | R_f |
|---|---|---|---|
| 12 | 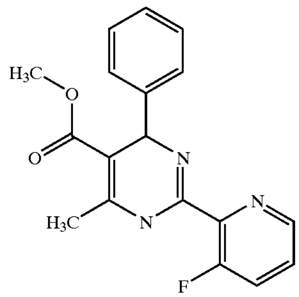 | 110–111 | — |
| 13 | x HCl | 222 decomposition | — |
| 14 | 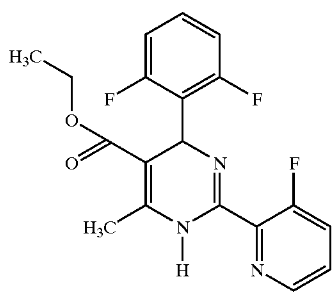 | 140–142 | — |
| 15 | 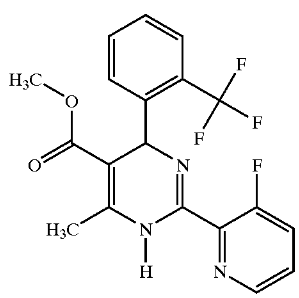 | 165–167 | — |
| 16 | 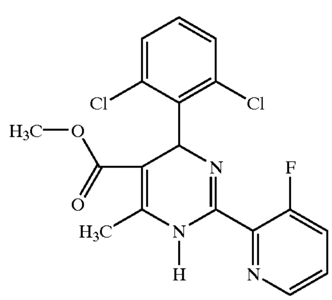 | 180–182 | — |

TABLE 1-continued

| Example No.: | Structure | m.p. [° C.] | R_f |
|---|---|---|---|
| 17 | 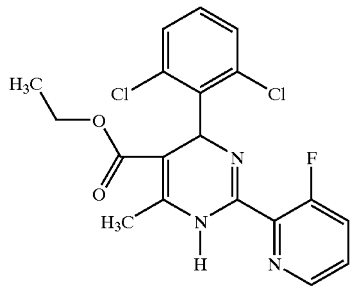 | 148–149 | — |
| 18 | 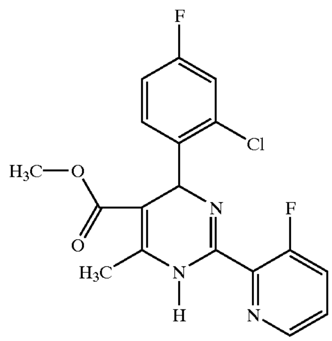 | 121–123 | — |
| 19 | 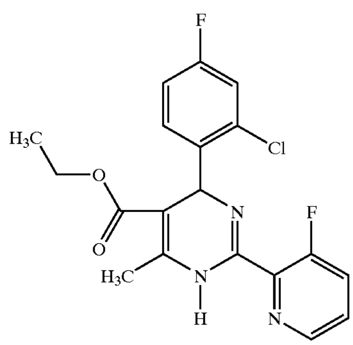 | 151–153 | — |
| 20 | 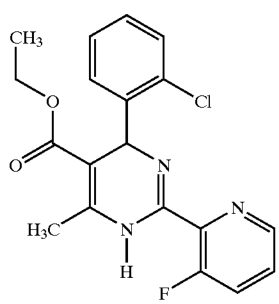 | 117–119 (−)-enantiomer of Example 4 | — |
| 21 | 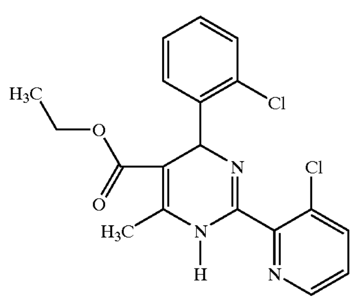 | 138–140 | — |

TABLE 1-continued

| Example No.: | Structure | m.p. [° C.] | R$_f$ |
|---|---|---|---|
| 22 | 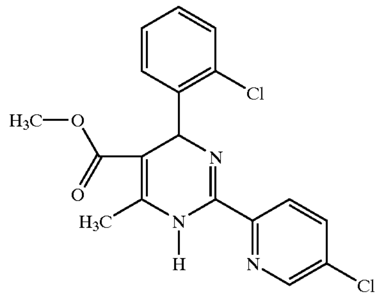 | 163–165 | — |
| 23 | 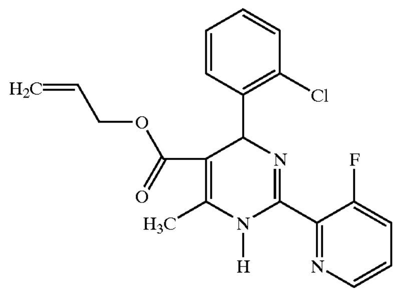 | 124–126 | — |
| 24 | 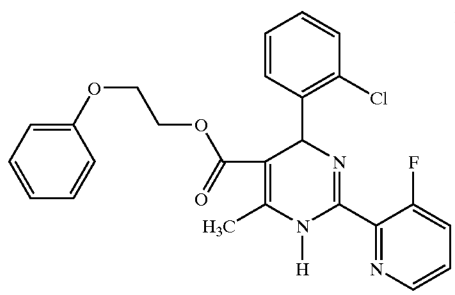 | 123–125 | — |
| 25 | 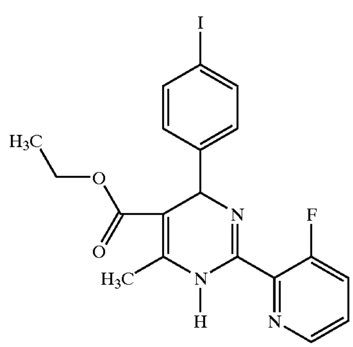 | 145–146 | — |
| 26 | 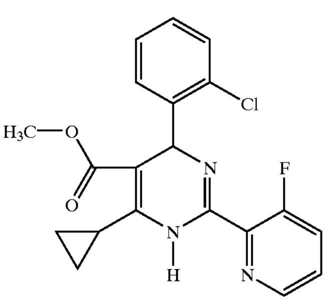 | 120–122 | — |

TABLE 1-continued

| Example No.: | Structure | m.p. [° C.] | $R_f$ |
|---|---|---|---|
| 27 | 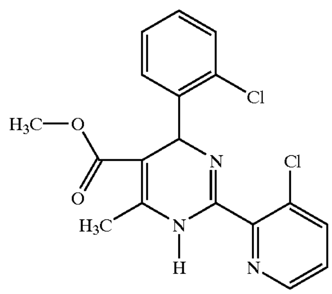 | 144–146 | — |
| 28 | 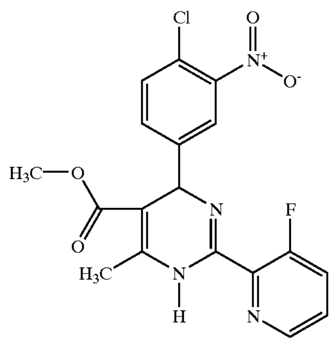 | 135–137 | — |
| 29 | 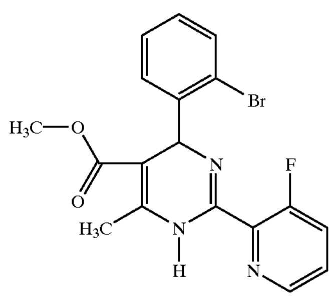 | 143–144 | — |
| 30 | 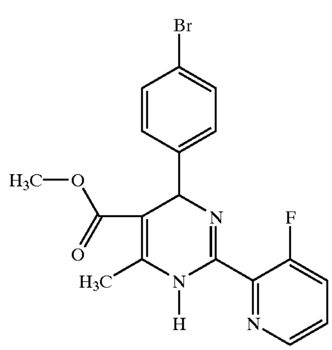 | 156–157 | — |

TABLE 1-continued

| Example No.: | Structure | m.p. [° C.] | R_f |
|---|---|---|---|
| 31 | 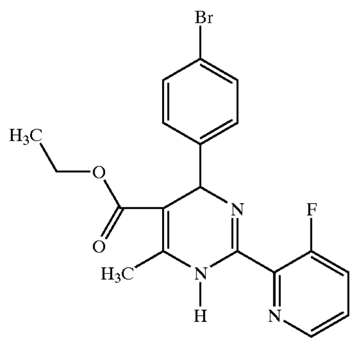 | 134–135 | — |
| 32 | 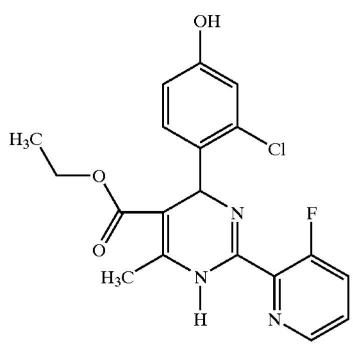 | 247–248 | — |
| 33 | 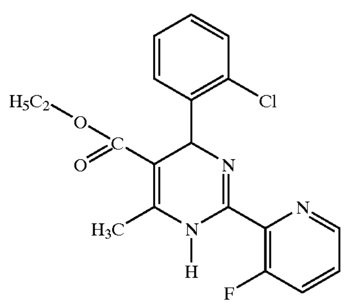 | 119–120 (−) enantiomer | — |
| 34 | 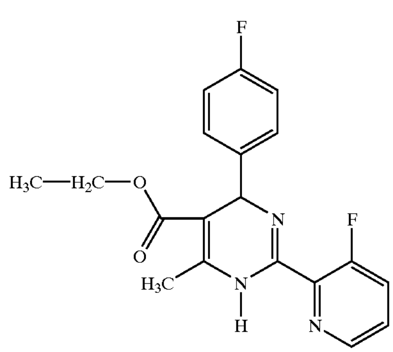 | 129–130° C. (−) enantiomer | — |

TABLE 1-continued

| Example No.: | Structure | m.p. [° C.] | $R_f$ |
|---|---|---|---|
| 35 | 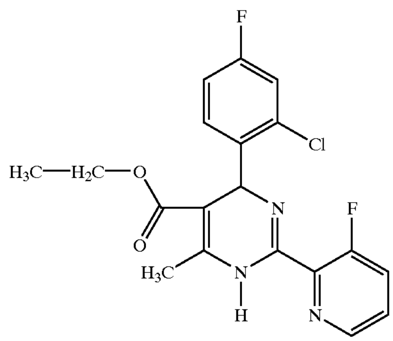 | (−) enantiomer of Ex. 19 | — |
| 36 | 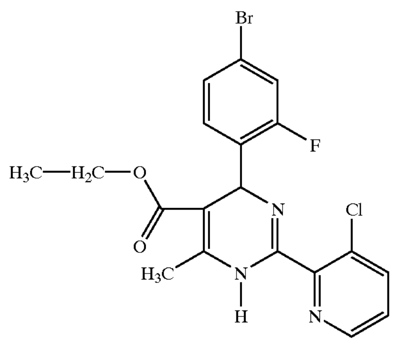 | 126–127 | — |
| 37 | 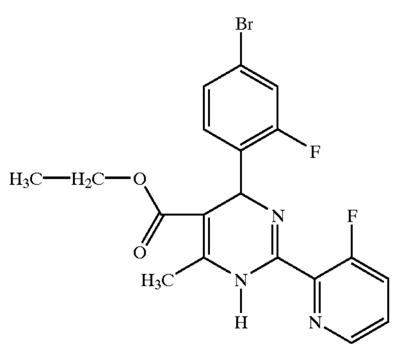 | 156–158 | — |
| 38 | 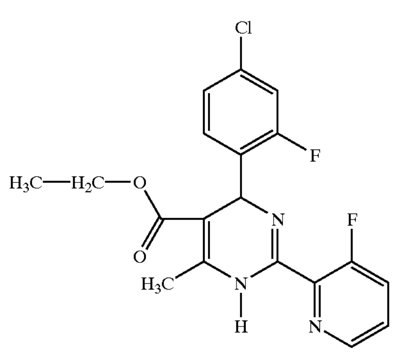 | 162–163 | — |

TABLE 1-continued
| Example No.: | Structure | m.p. [° C.] | R_f |
|---|---|---|---|
| 39 | 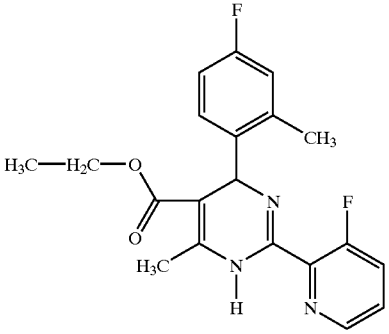 | 167–169 | — |
| 40 | 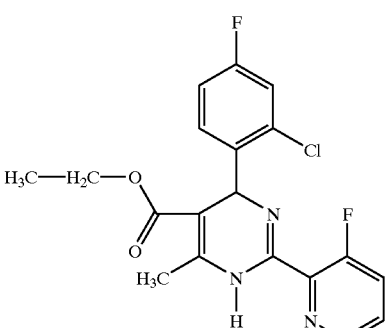 | 129–130 | — |
| 41 | 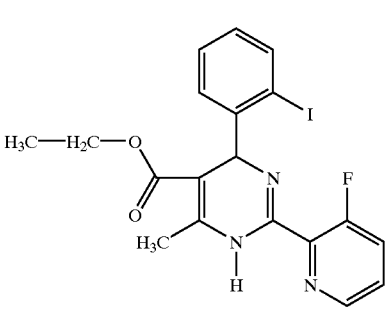 | 163–164 | — |
| 42 | 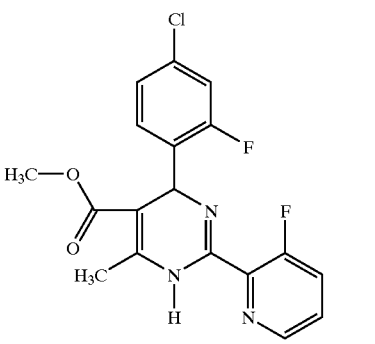 | 120–122 | — |

TABLE 1-continued

| Example No.: | Structure | m.p. [° C.] | R$_f$ |
|---|---|---|---|
| 43 | 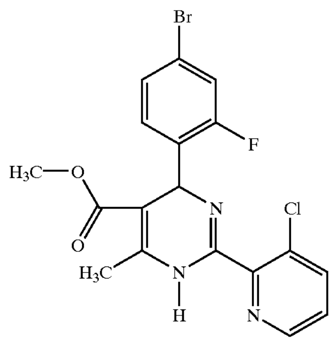 | 103–104 | — |
| 44 | 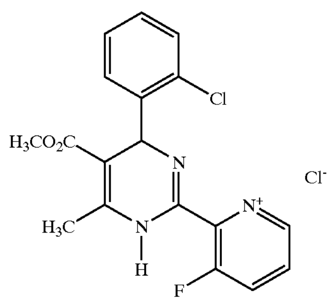 | 210–212 | — |
| 45 | 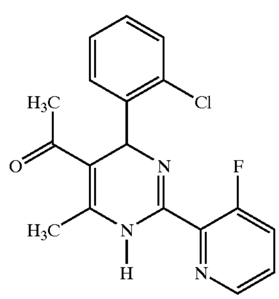 | 132–133° C. | — |
| 46 | 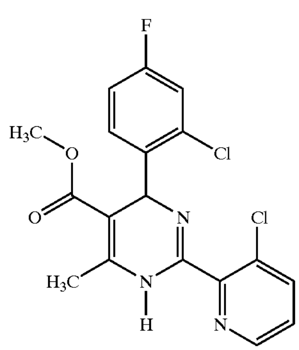 | 95–96° C. | — |

TABLE 1-continued

| Example No.: | Structure | m.p. [° C.] | $R_f$ |
|---|---|---|---|
| 47 | 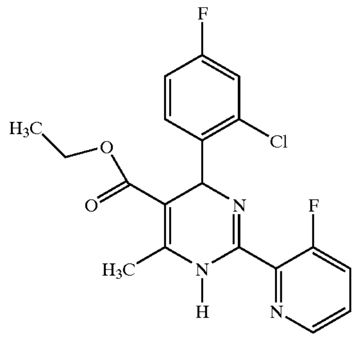 | 154–155° C. | — |
| 48 | 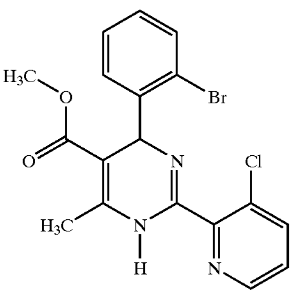 | 131–132° C. | — |
| 49 | 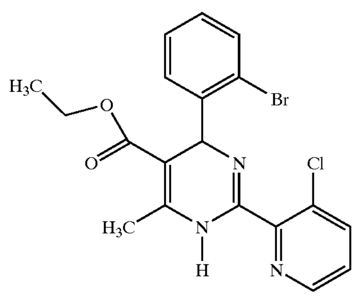 | 137–138° C. | — |
| 50 | 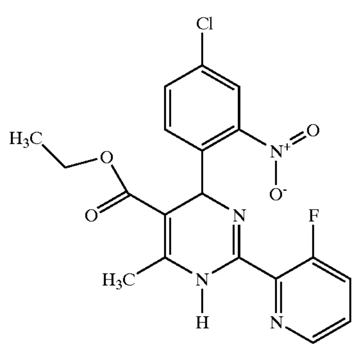 | 184–186° C. | — |
| 51 | 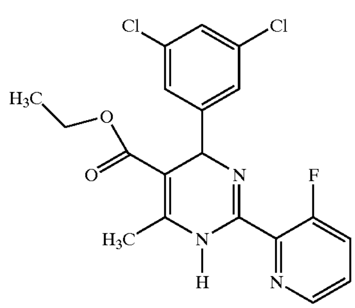 | 133–134° C. | — |

TABLE 1-continued

| Example No.: | Structure | m.p. [° C.] | R$_f$ |
|---|---|---|---|
| 52 | (structure) | 135–136° C. | — |
| 53 | (structure) | 131° C. | — |
| 54 | (structure) | amorphous | 0.17 (cyclohexane/ethyl acetate = 7:3) |
| 55 | (structure) | 124° C. | — |

TABLE 1-continued

| Example No.: | Structure | m.p. [° C.] | R_f |
|---|---|---|---|
| 56 | 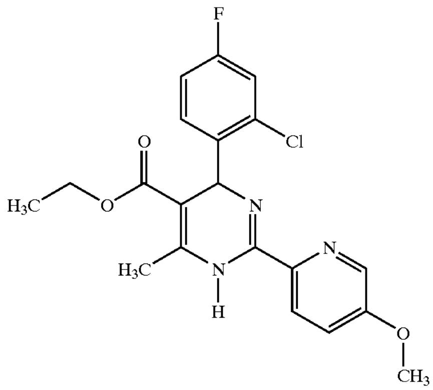 | 141° C. | — |
| 57 | 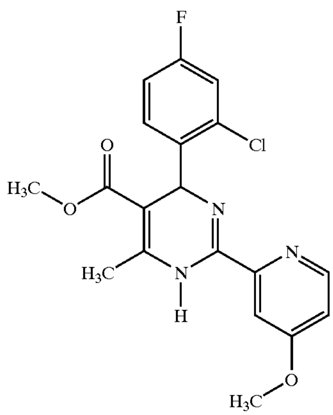 | 132° C. | — |
| 58 | 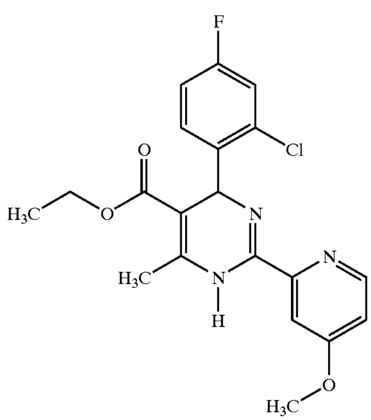 | amorphous | 0.14 (cyclohexane/-ethyl acetate = 7:3) |
| 59 | 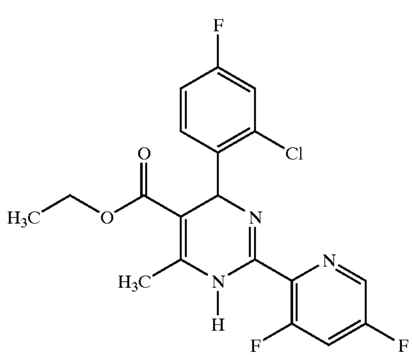 | amorphous | 0.23 (cyclohexane/ethyl acetate = 7:3) |

TABLE 1-continued

| Example No.: | Structure | m.p. [° C.] | R_f |
|---|---|---|---|
| 60 | 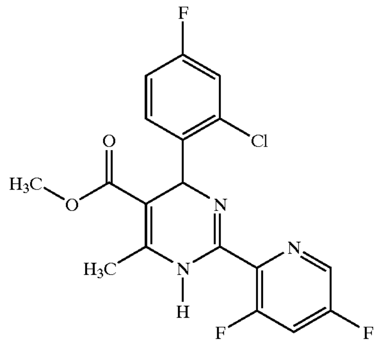 | 126° C. | — |

EXAMPLE 61

Methyl 4-(2-Chloro-4-fluorophenyl)-2-(3,5-difluoro-2-pyridinyl)-6-methyl-1,4-dihydropyrimidine-5-carboxylate (See Table)

4.5 g (23.2 mmol) of 3,5-difluoro-2-pyridinecarboximidamide hydrochloride (Example VI) with 7.7 g (30 mmol) of methyl 2-acetyl-3-(2-chloro-4-fluorophenyl)-2-propenoate (Example VII) and 2.3 g (27.9 mmol) of sodium acetate are dissolved or suspended in 120 ml of isopropanol and boiled under reflux for 4 h.

The mixture is cooled to room temperature and then filtered off with suction from inorganic salts and concentrated. The residue is taken up in 30 ml of 1N HCl and 35 ml of ethyl acetate, and the phases are separated. The ethyl acetate phase is re-extracted once using 30 ml of 1N HCl. The combined aqueous phases are extracted three times with 10 ml of diethyl ether each time. The aqueous phase is made alkaline using NaOH and extracted with ethyl acetate. The organic phases are dried over $Na_2SO_4$ and concentrated.

This gives 7.4 g (80%) of product. (m.p.: 126° C.)

$^1$H-NMR (DMSO-$D_6$): 2.4(s, 3H), 3.5(s, 3H), 6.0(s, 1H), 7.2(m, 1H), 7.4(m, 2H), 8.0(m, 1H), 8.55(d, J=2 Hz, 1H), 9.75(s, NH) ppm.

The (−)-enantiomer was obtained after separation of the enantiomers on chiral columns (Chiralpak AS from Baker, mobile phase n-heptane/ethanol=8:2).

m.p.: 117° C. (from ethanol); Spec. rot.: −62.8° (MeOH).

TABLE 2

| Example No.: | Structure | [M + H] | MS ES + |
|---|---|---|---|
| 61 | 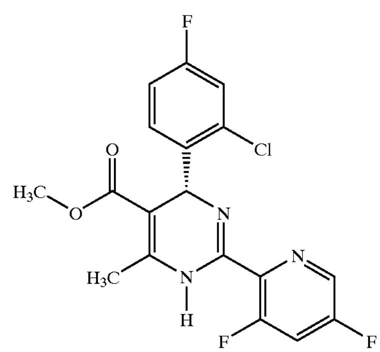 | 117° C. (ethanol) (−)-enantiomer | — |
| 62 | 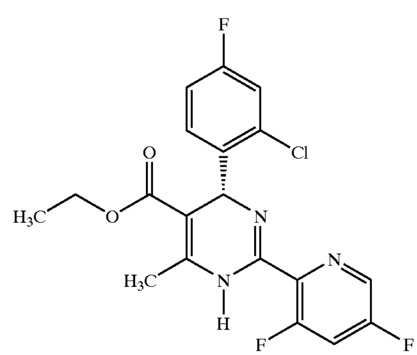 | amorphous (−)-enantiomer | 0.23 (cyclohexane/ethyl acetate = 7:3) |

TABLE 2-continued

| Example No.: | Structure | [M + H] | MS ES + |
|---|---|---|---|
| 63 | 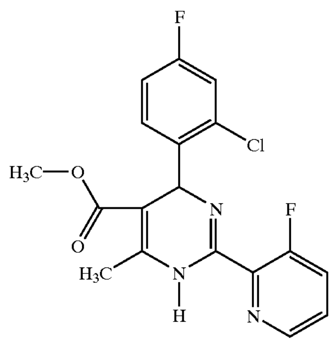 | amorphous | 0.36 (toluene/ethyl acetate = 1:1) (−)-enantiomer |
| 64 | 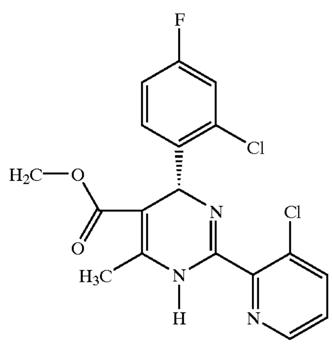 | 119–120° C. (−)-enantiomer | |
| 65 | 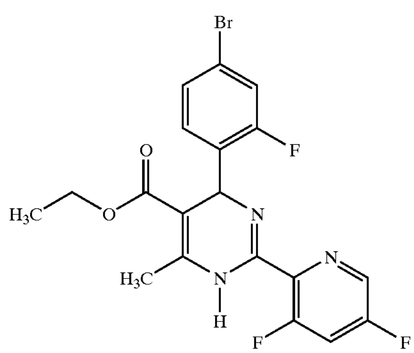 | 159° C. | — |
| 66 | 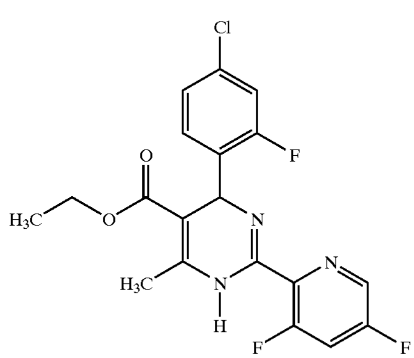 | 154° C. | — |

TABLE 2-continued

| Example No.: | Structure | [M + H] | MS ES + |
|---|---|---|---|
| 67 | 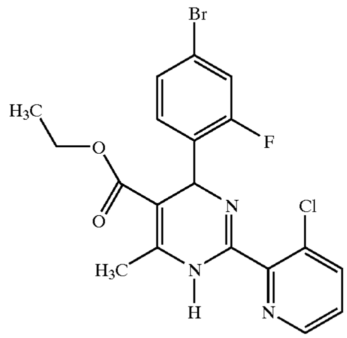 | amorphous | 0.33 (toluene/ethyl acetate = 1:1) (−)-enantiomer |
| 68 | 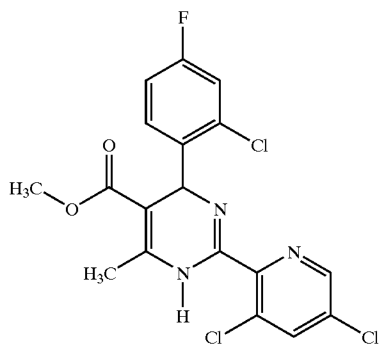 | amorphous | 0.30 (cyclohexane/ethyl acetate = 7:3) |
| 69 | 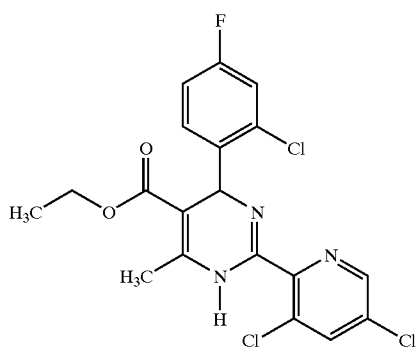 | 152° C. | 0.35 (cyclohexane/ethyl acetate = 7:3) |
| 70 | 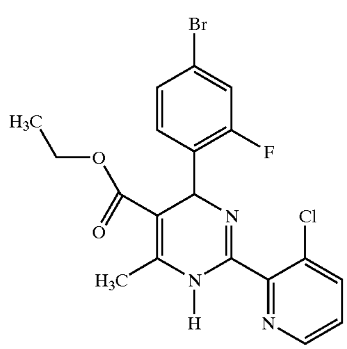 | amorph | 0.33 (toluene/-ethyl acetate = 1:1) |

TABLE 2-continued

| Example No.: | Structure | [M + H] | MS ES + |
|---|---|---|---|
| 71 | 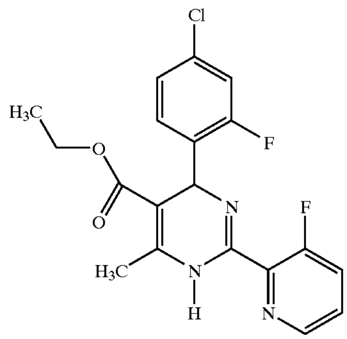 | 91–93° C. (−) enantiomer | |
| 72 | 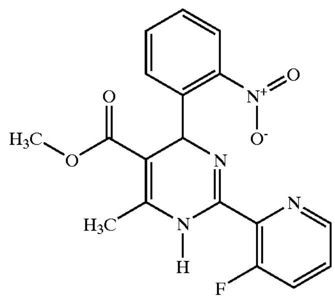 | amorphous | 0.20 (cyclohexane/ethyl acetate = 1:1) |
| 73 | 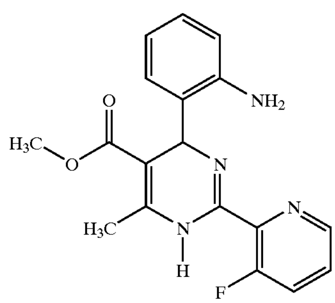 | amorphous | 0.27 (CH$_2$Cl$_2$/ MeOH = 95:5) |
| 74 | 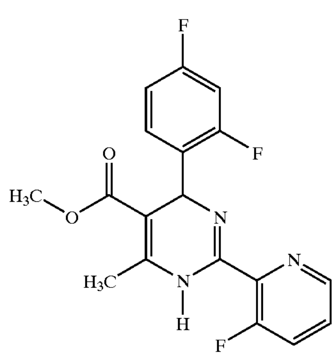 | 362 | |

TABLE 2-continued

| Example No.: | Structure | [M + H] MS ES + |
|---|---|---|
| 75 | 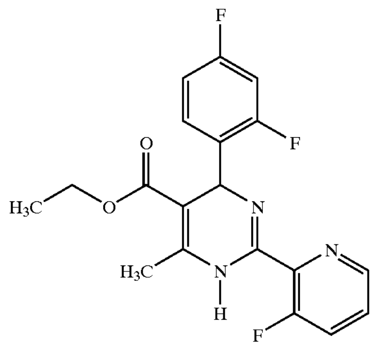 | 376 |
| 76 | 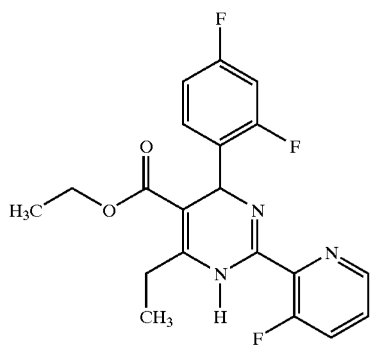 | 371 |
| 77 | 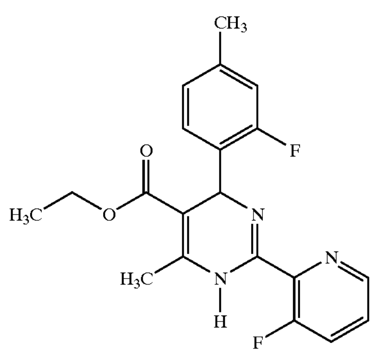 | 372 |
| 78 | 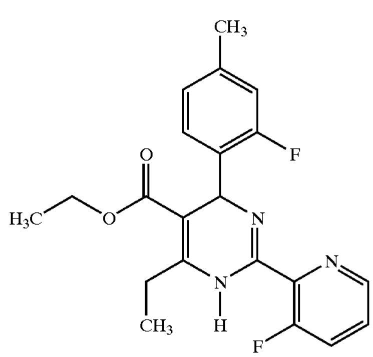 | 385 |

TABLE 2-continued

| Example No.: | Structure | [M + H] | MS ES + |
|---|---|---|---|
| 79 | 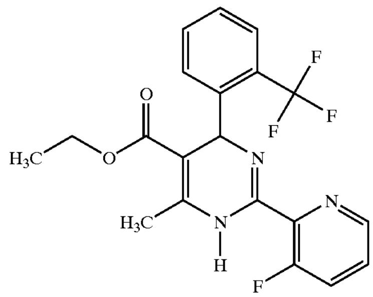 | 408 | |
| 80 | 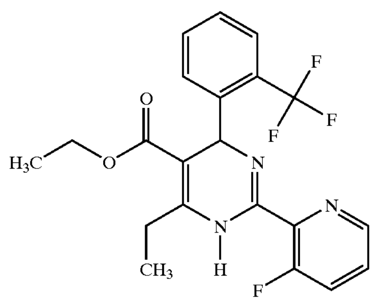 | 421 | |
| 81 | 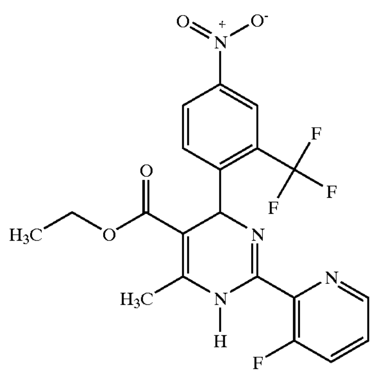 | 453 | |
| 82 | 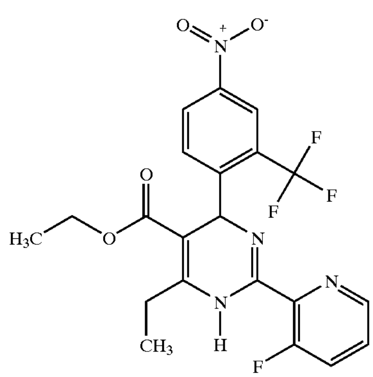 | 466 | |

TABLE 2-continued

| Example No.: | Structure | [M + H] | MS ES + |
|---|---|---|---|
| 83 | 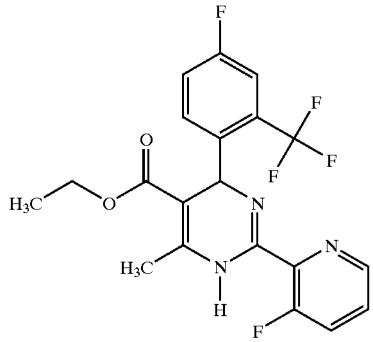 | | 425 |
| 84 | | | 371 | m.p.[° C.] = melting point in degrees Celsius

What is claimed is:

1. A compound of the general formula (I)

(I)

or its isomeric form (Ia)

(Ia)

in which

R$^1$ represents phenyl, furyl, thienyl, triazolyl, pyridyl, cycloalkyl having 3 to 6 carbon atoms or represents radicals of the formulae

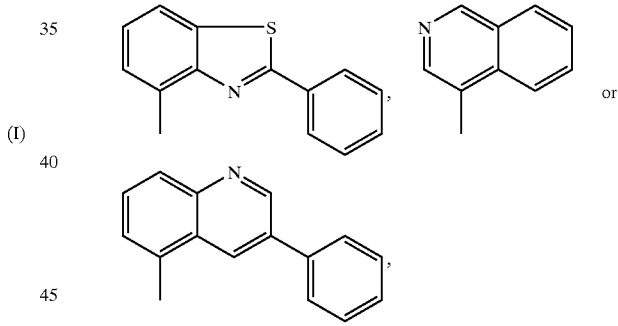

where the abovementioned ring systems are optionally mono- or polysubstituted by identical or different substituents selected from the group consisting of halogen, trifluoromethyl, nitro, cyano, trifluoromethoxy, carboxyl, hydroxyl, (C$_1$–C$_6$)-alkoxy, (C$_1$–C$_6$)-alkoxycarbonyl and (C$_1$–C$_6$)-alkyl, which for its part may be substituted by aryl having 6 to 10 carbon atoms or halogen, and/or the ring systems mentioned are optionally substituted by groups of the formulae —S—R$^6$, NR$^7$R$^8$, CO—NR$^9$R$^{10}$, SO$_2$—CF$_3$ and —A—CH$_2$—R$^{11}$, in which R$^6$ represents phenyl which is optionally substituted by halogen, R$^7$, R$^8$, R$^9$ and R$^{10}$ are identical or different, and each represents hydrogen, phenyl, hydroxyl-substituted phenyl, hydroxyl, (C$_1$–C$_6$)-acyl or (C$_1$–C$_6$)-alkyl, which for its part may be substituted by hydroxyl, (C$_1$–C$_6$)-alkoxycarbonyl, phenyl or hydroxyl-substituted phenyl, A represents a radical O, S, SO or S$_2$O, R$^{11}$ represents phenyl which is optionally mono- to polysubstituted by identical or different substituents selected from the group consisting of halogen, nitro, trifluoromethyl, (C$_1$–C$_6$)-alkyl and (C$_1$–C$_6$)-alkoxy, R$^2$ represents a radical of the formula —XR$^{12}$ or —NR$^{13}$R$^{14}$, in which X represents a bond or oxygen, R$^{12}$ represents hydrogen straight-chain or branched (C$_1$–C$_6$)-alkoxycarbonyl or a straight-chain, branched or cyclic saturated or unsaturated (C$_1$–C$_8$)-hydrocarbon radical which optionally contains one or two identical or different hetero chain members from the group consisting of O, CO, NH, —NH—(C$_1$–C$_4$)-alkyl, —N—((C$_1$–C$_4$)-alkyl)$_2$, S and S$_2$O and which is optionally substituted by halogen, nitro, cyano, hydroxyl, aryl having 6 to 10 carbon atoms or aralkyl having 6 to 10 carbon atoms, heteroaryl or a group of the formula —NR$^{15}$R$^{16}$, in which R$^{15}$ and R$^{16}$ are identical or different, and each represents hydrogen, benzyl or (C$_1$–C$_6$)-alkyl, R$^{13}$ and R$^{14}$ are identical or different, and each represents hydrogen, (C$_1$–C$_6$)-alkyl or cycloalkyl having 3 to 6-carbon atoms, R$^3$ represents hydrogen, amino or represents a radical of the formula

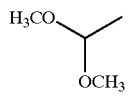

or represents formyl, cyano, trifluoromethyl or pyridyl, or represents a straight-chain, branched or cyclic saturated or unsaturated hydrocarbon radical having up to 8 carbon atoms which is optionally mono- or polysubstituted by identical or different substituents from the group consisting of aryloxy having 6 to 10 carbon atoms, azido, cyano, hydroxyl, carboxyl, (C$_1$–C$_6$)-alkoxycarbonyl, a 5- to 7-membered heterocyclic ring, (C$_1$–C$_6$)-alkylthio and (C$_1$–C$_6$)-alkoxy, which for its part may be substituted by azido or amino, and/or is substituted by triazolyl, which for its part may be substituted up to 3 times by (C$_1$–C$_6$)-alkoxycarbonyl, and/or may be substituted by groups of the formulae —OSO$_2$—CH$_3$ or (CO)$_a$—NR$^{17}$R$^{18}$, in which a represents a number 0 or 1, R$^{17}$ and R$^{18}$ are identical or different, and each represents hydrogen or aryl, aralkyl having 6 to 10 carbon atoms, or represents (C$_1$–C$_6$)-alkyl which is optionally substituted by (C$_1$–C$_6$)-alkoxycarbonyl, hydroxyl, phenyl or benzyl, where phenyl or benzyl are optionally mono- or polysubstituted by identical or different substituents from the group consisting of hydroxyl, carboxyl, (C$_1$–C$_6$)-alkyl and (C$_1$–C$_6$)-alkoxy, or (C$_1$–C$_6$)-alkyl is optionally substituted by groups of the formulae NH—CO—CH$_3$ or NH—CO—CF$_3$, or R$^{17}$ and R$^{18}$ together with the nitrogen atom form a morpholine, piperidinyl or pyrrolidinyl ring, or R$^3$ represents phenyl which is optionally substituted by methoxy, or R$^2$ and R$^3$ together form a radical of the formula

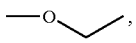

R$^4$ represents hydrogen, (C$_1$–C$_4$)-alkyl, (C$_2$–C$_4$)-alkenyl, benzoyl or represents acyl having 2 to 6 carbon atoms, R$^5$ represents pyridyl which is substituted 1 to 3 times by identical or different substituents from the group consisting of halogen, hydroxyl, cyano, trifluoromethyl, (C$_1$–C$_6$)-alkoxy, (C$_1$–C$_6$)-alkyl, (C$_1$–C$_6$)-alkylthio, carbalkoxy, (C$_1$–C$_6$)-acyloxy, amino, nitro, mono- and (C$_1$–C$_6$)-dialkylamino, or a salt thereof.

2. A compound of the general formulae (I) and (Ia) according to claim 1, in which R$^1$ represents phenyl, furyl, thienyl, pyridyl, cyclopentyl or cyclohexyl or represents radicals of the formulae

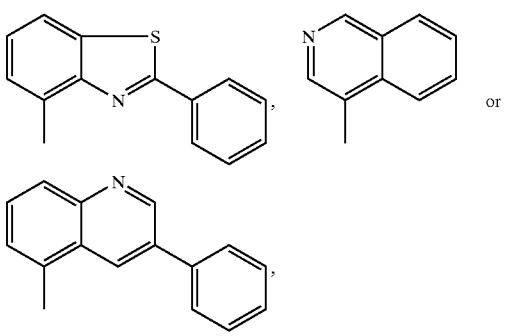

where the abovementioned ring systems are optionally mono- or disubstituted by identical or different substituents selected from the group consisting of halogen, trifluoromethyl, nitro, SO$_2$—CF$_3$, methyl, cyano, amino, trifluoromethoxy, hydroxyl, carboxyl, methoxycarbonyl and radicals of the formulae —CO—NH—CH$_2$—C(CH$_3$)$_3$, —CO—NH(CH$_2$)$_2$OH, —CO—NH—CH$_2$—C$_6$H$_5$, —CO—NH—C$_6$H$_5$, —CO—NH—(pOH)—C$_6$H$_4$, —O—CH$_2$—C$_6$H$_5$ or —S—pCl—C$_6$H$_4$, R$^2$ represents a radical of the formula —XR$^{12}$ or —NR$^{13}$R$^{14}$, in which X represents a bond or an oxygen atom, R$^2$ represents hydrogen, (C$_1$–C$_4$)-alkenyl, (C$_1$–C$_4$)-alkoxycarbonyl or (C$_1$–C$_4$)-alkyl which are optionally substituted by pyridyl, cyano, phenoxy, benzyl or by a radical of the formula —NR$^{15}$R$^{16}$, in which R$^{15}$ and R$^{16}$ are identical or different, and each represents hydrogen, benzyl or (C$_1$–C$_4$)-alkyl, R$^{13}$ and R$^{14}$ are identical or different, and each represents hydrogen, (C$_1$–C$_4$)-alkyl or cyclopropyl, R$^3$ represesents hydrogen, amino or a radical of the formula

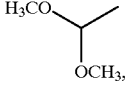

or represents formyl, cyano, trifluoromethyl, cyclopropyl or pyridyl, or represents (C$_1$–C$_4$)-alkyl which is optionally substituted by halogen, (C$_1$–C$_4$)-alkoxycarbonyl, hydroxyl or by triazolyl, which for its part may be substituted up to 3 times by $(C_1-C_4)$-alkoxycarbonyl, and/or alkyl is optionally substituted by groups of the formulae —OSO$_2$—CH$_3$ or (CO)$_a$—NR$^{17}$R$^{18}$, in which a represents a number 0 or 1, $R^{17}$ and $R^{18}$ are identical or different, and each represents hydrogen, phenyl or benzyl, or represents $C_1-C_4$-alkyl which is optionally substituted by $(C_1-C_4)$-alkoxycarbonyl, hydroxyl, phenyl or benzyl, where phenyl or benzyl are optionally mono- or polysubstituted by identical or different substitutents from the group consisting of hydroxyl, carboxyl, $(C_1-C_4)$-alkyl and $(C_1-C_4)$-alkoxy, and/or $(C_1-C_4)$-alkyl is optionally substituted by radicals of the formulae —NH—CO—CH$_3$ or —NH—CO—CF$_3$, or $R^{17}$ and $R^{18}$ together with the nitrogen atom form a morpholine, piperidinyl or pyrrolidinyl ring, or $R^3$ represents phenyl which is optionally substituted by methoxy, or $R^2$ and $R^3$ together form a radical of the formula

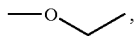

$R^4$ represents hydrogen, methyl, benzoyl or acetyl, $R^5$ represents pyridyl which is substituted 1 to 2 times by identical or different substituents from the group consisting of fluorine, chlorine, bromine, $(C_1-C_4)$-alkoxy and $(C_1-C_4)$-alkyl, or a salt thereof.

3. A compound of the general formulae (I) and (Ia) according to claim 1 in which $R^1$ represents phenyl, furyl, thienyl, pyridyl, cyclopentyl, cyclohexyl or represents radicals of the formulae

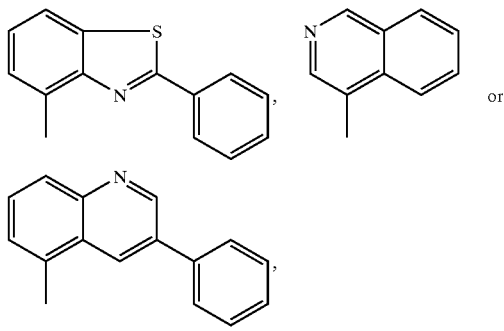

where the abovementioned ring systems are optionally substituted up to 2 times by identical or different substituents selected from the group consisting of fluorine, chlorine, bromine, iodine, hydroxyl, trifluoromethyl, amino, nitro, SO$_2$—CF$_3$, methyl, cyano, trifluoromethoxy, carboxyl, methoxycarbonyl and radicals of the formulae —CO—NH—CH$_2$—C(CH$_3$)$_3$, —CO—NH(CH$_2$)$_2$OH, —CO—NH—CH$_2$—C$_6$H$_5$, —CO—NH—C$_6$H$_5$, —CO—NH—(pOH)—C$_6$H$_4$, —O—CH$_2$—C$_6$H$_5$ or —S—pCl—C$_6$H$_4$, $R^2$ represents a radical of the formula —XR$^{12}$ or —NR$^{13}$R$^{14}$, in which X represents a bond or an oxygen atom, $R^{12}$ represents hydrogen, $(C_1-C_3)$-alkenyl, $(C_1-C_4)$-alkoxycarbonyl or $(C_1-C_4)$-alkyl which are optionally substituted by pyridyl, cyano, phenoxy, benzyl or by a radical of the formula —NR$^{15}$R$^{16}$, in which $R^{15}$ and $R^{16}$ are identical or different, and each represents hydrogen or methyl, $R^{13}$ and $R^{14}$ are identical or different, and each represents hydrogen, $(C_1-C_3)$-alkyl or cyclopropyl, $R^3$ represents hydrogen, amino or represents a radical of the formula

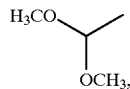

or represents formyl, cyano, trifluoromethyl, cyclopropyl or pyridyl, or represents $(C_1-C_4)$-alkyl which is optionally substituted by fluorine, chlorine, $(C_1-C_3)$-alkoxycarbonyl, hydroxyl or by triazolyl, which for its part may be substituted up to 3 times by $(C_1-C_3)$-alkoxycarbonyl, and/or alkyl is optionally substituted by groups of the formulae —OSO$_2$—CH$_3$ or (CO)$_{a-NR}$$^{17}$R$^{18}$, in which a represents a number 0 or 1, $R^{17}$ and $R^{18}$ are identical or different, and each represents hydrogen, phenyl or benzyl, or represents $(C_1-C_3)$-alkyl which is optionally substituted by $(C_1-C_3)$-alkoxycarbonyl, hydroxyl, phenyl or benzyl, where phenyl or benzyl are optionally mono- or disubstituted by identical or different substituents from the group consisting of hydroxyl, carboxyl, $(C_1-C_3)$-alkyl and $(C_1-C_3)$-alkoxy, and/or $(C_1-C_4)$-alkyl is optionally.substituted by radicals of the formulae —NH—CO—CH$_3$ or —NH—CO—CF$_3$, or $R^{17}$ and $R^{18}$ together with the nitrogen atom form a morpholine, piperidinyl or pyrrolidinyl ring, or $R^3$ represents phenyl which is optionally substituted by methoxy, or $R^2$ and $R^3$ together form a radical of the formula

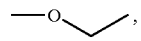

$R^4$ represents hydrogen, methyl, benzoyl or acetyl, $R^5$ represents pyridyl which is substituted 1 to 2 times by identical or different substituents from the group consisting of fluorine, chlorine, $(C_1-C_3)$-alkoxy and $(C_1-C_3)$-alkyl, or a salt thereof.

4. A compound of the general formulae (I) and (Ia) according to claim 1, in which $R^1$ represents phenyl which is optionally substituted up to 2 times by identical or different substituents from the group consisting of fluorine, chlorine, bromine, iodine, methyl and nitro, $R^2$ represents —XR$^{12}$ in which X represents oxygen and $R^{12}$ represents straight-chain or branched alkyl having up to 4 carbon atoms, $R^3$ represents methyl, ethyl or cyclopropyl, or R² and R³ together form a radical of the formula

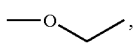

R⁴ represents hydrogen, or acetyl, and
R⁵ represents pyridyl which is substituted one to two times by identical or different substituents from the group consisting of fluorine and chlorine,
or a salt thereof.

5. A compound of the general formulae (I) and (Ia) according to claim 1 in which R⁵ represents 2-pyridyl which is substituted by 1 or 2 fluorine atoms.

6. A compound according to claim 1 of the structures below

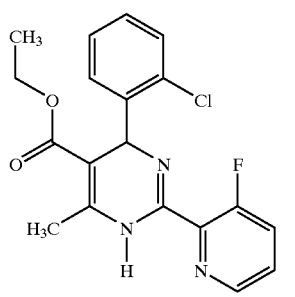

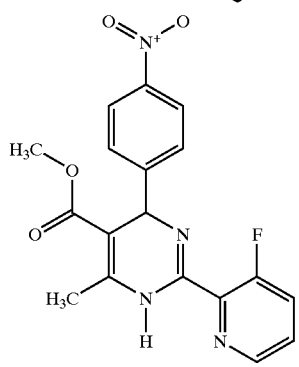

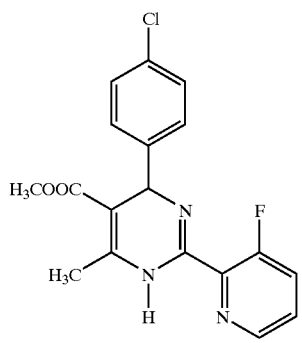

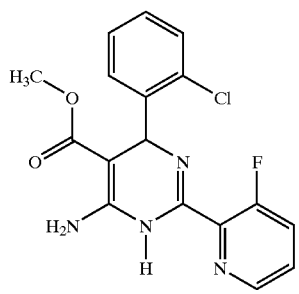

-continued

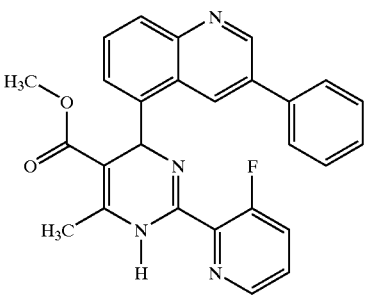

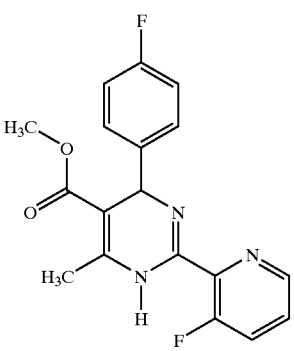

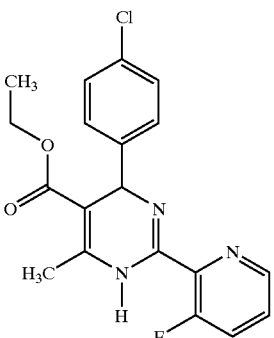

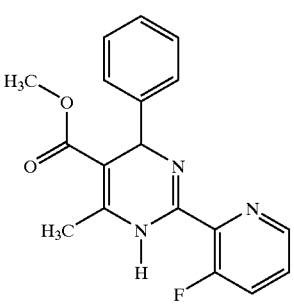

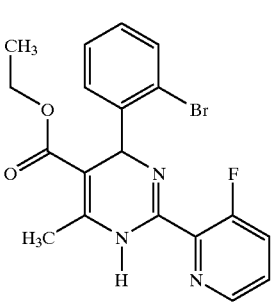

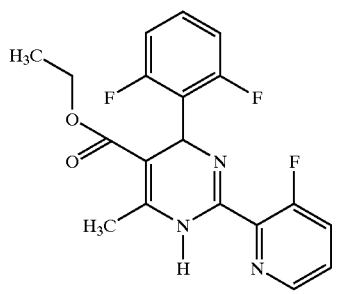
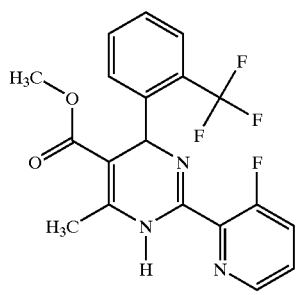
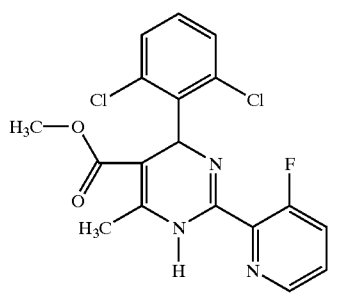
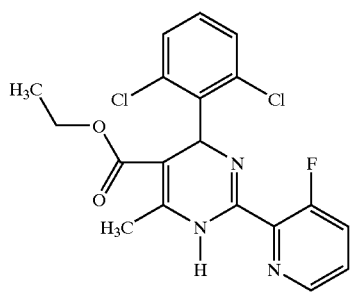
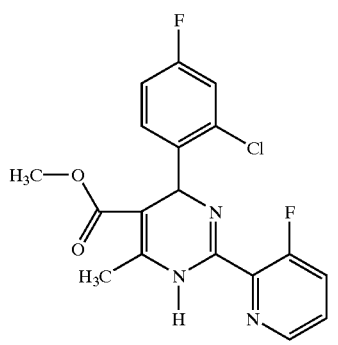
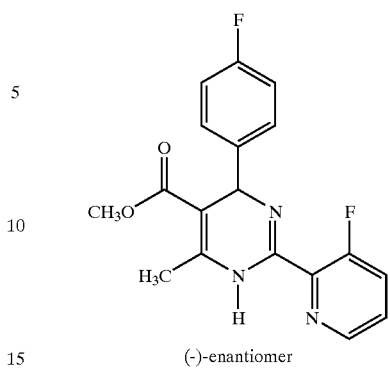
(-)-enantiomer
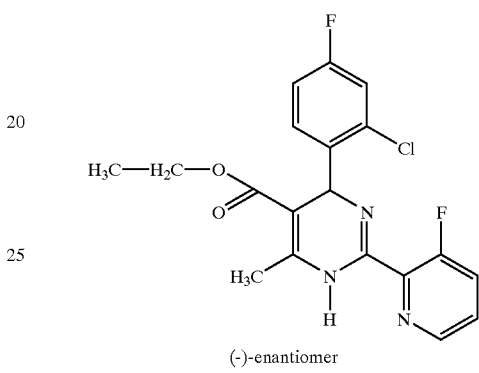
(-)-enantiomer
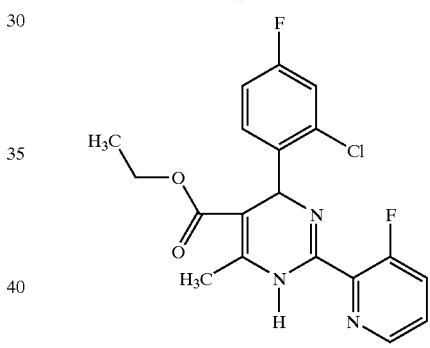
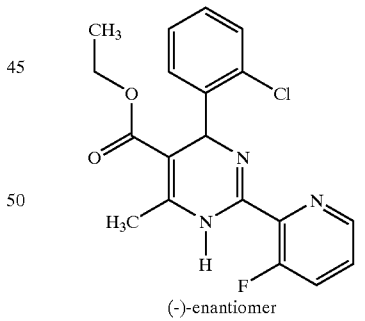
(-)-enantiomer
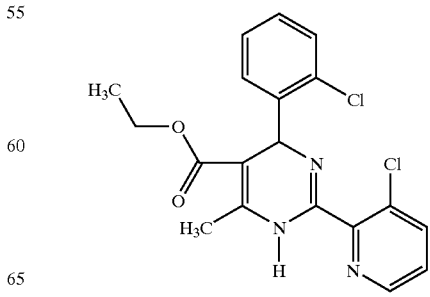

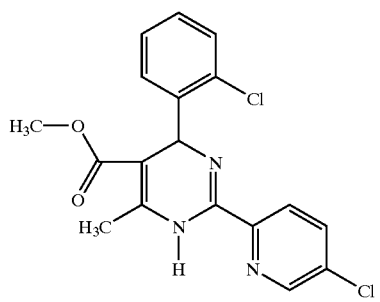
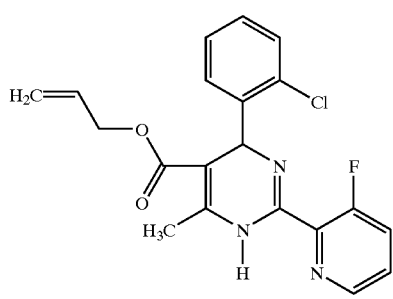
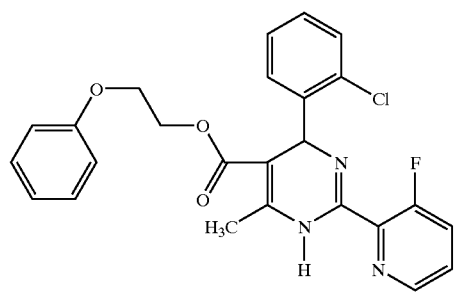
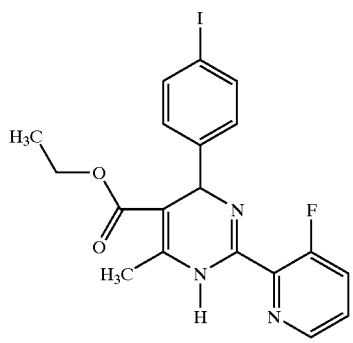
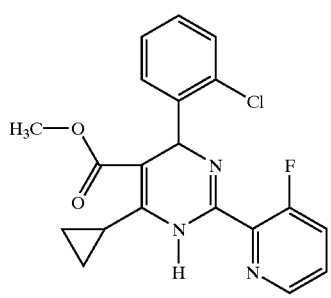
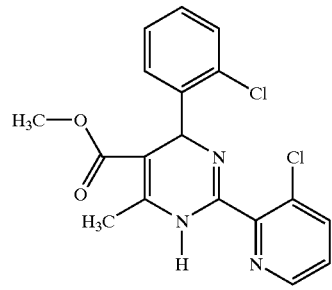
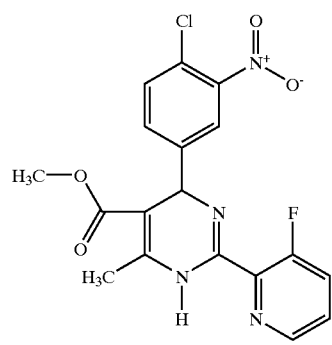
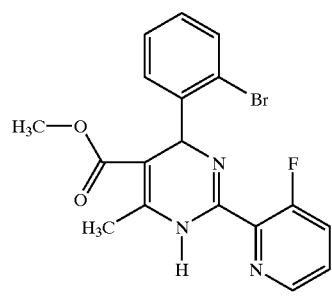
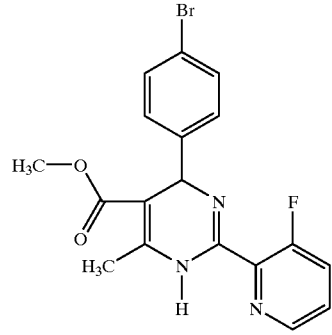
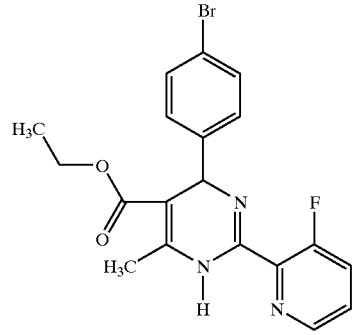

-continued
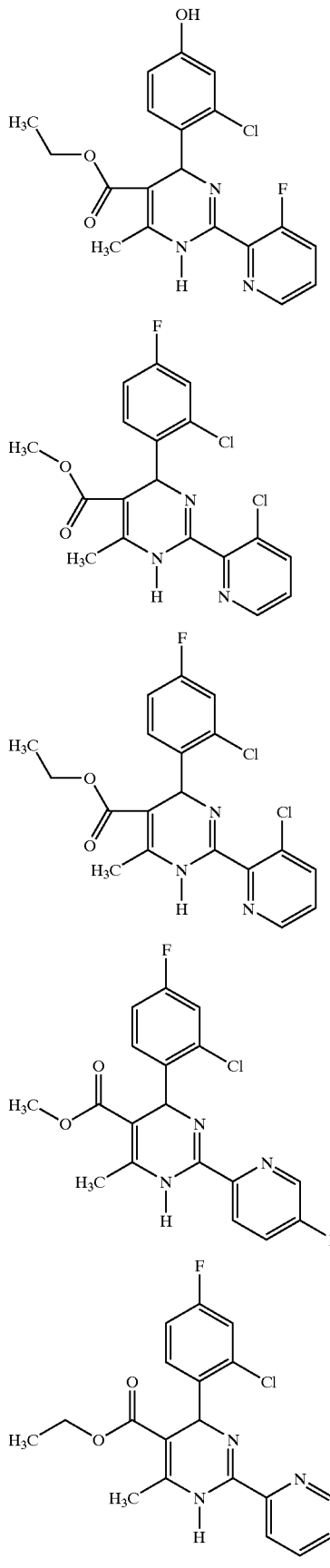
-continued
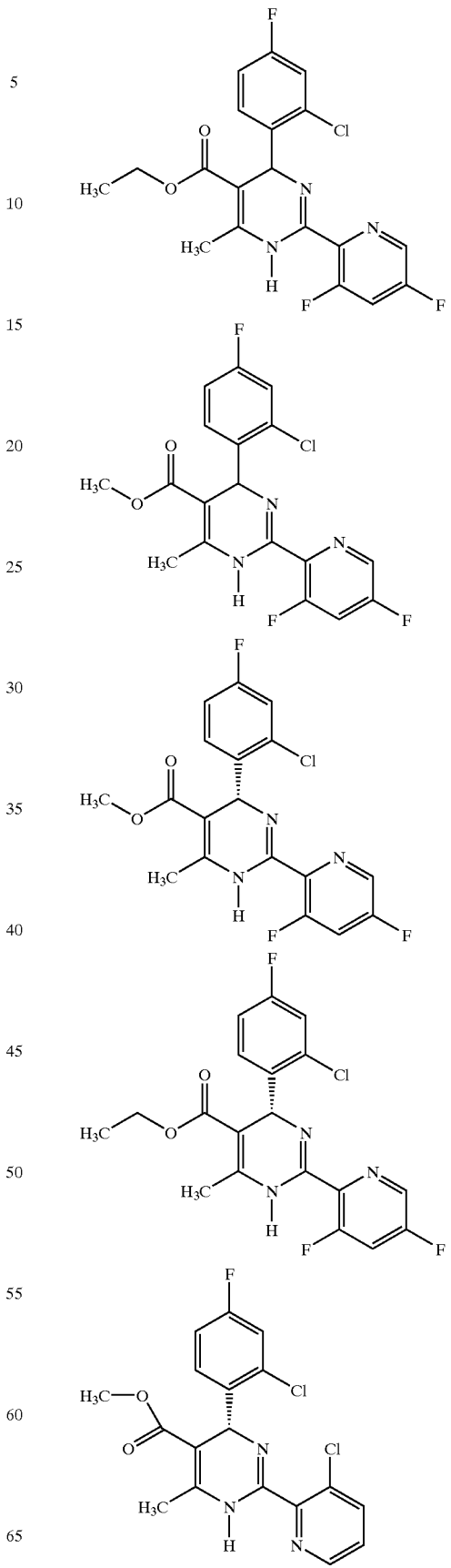

-continued

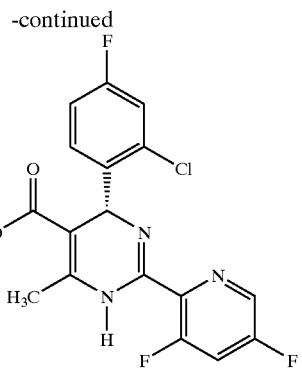

And

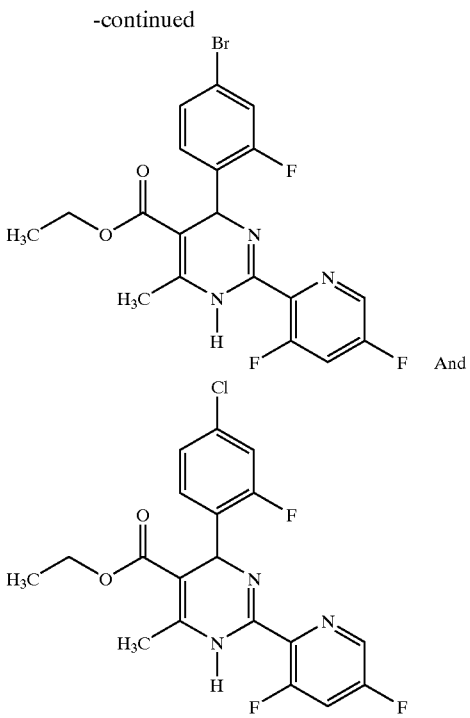

7. A compound according to claim 1 of the structures below:

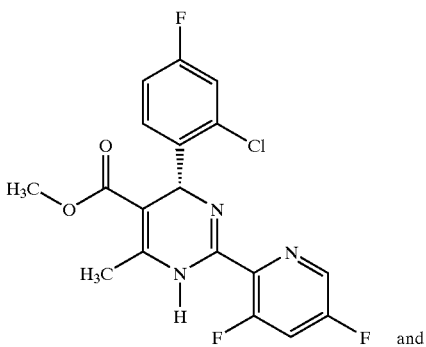

and

-continued

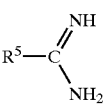

or a salt thereof.

8. A process for preparing a compound of claim 1, comprising reacting an aldehyde of the general formula (II)

$$R^1—CHO \quad (II)$$

in which
 $R^1$ is as defined above in claim 1,
with an amidine or its hydrochloride of the formula (III)

$$R^5—C(=NH)NH_2 \quad (III)$$

in which
 $R^5$ is as defined above in claim 1,
and a compound of the general formula (IV)

$$R^3—CO—CH_2—CO—R^2 \quad (IV)$$

in which
 $R^2$ and $R^3$ are each as defined above in claim 1.

9. A medicament, containing at least one compound of the general formula (I) or (Ia) according to claim 1.

10. A medicament of claim 9, further comprising another pharmaceutically active compound.

11. A process for producing medicaments, characterized in that at least one compound of the general formula (I) or (Ia) according to claim 1 is converted into a suitable administration form by the addition of customary auxiliaries and excipients.

12. A method of treating an acute or chronic hepatitis B infection, comprising administering to a patient in need thereof an effective amount of a compound according to claim 1.

* * * * *